US012579905B2

(12) United States Patent
Ahmad et al.

(10) Patent No.: US 12,579,905 B2
(45) **Date of Patent: *Mar. 17, 2026**

(54) ARTIFICIAL INTELLIGENCE BASED HEALTH COACHING BASED ON BREATH ANALYTE LEVELS OF PARTICIPANTS

(71) Applicant: Invoy Holdings Inc., Irvine, CA (US)

(72) Inventors: Lubna M. Ahmad, Chandler, AZ (US); Salman A. Ahmad, Chandler, AZ (US)

(73) Assignee: Invoy Holdings Inc., Irvine, CA (US)

( * ) Notice: Subject to any disclaimer, the term of this patent is extended or adjusted under 35 U.S.C. 154(b) by 935 days.

This patent is subject to a terminal disclaimer.

(21) Appl. No.: 17/498,571

(22) Filed: Oct. 11, 2021

(65) Prior Publication Data

US 2022/0130277 A1 Apr. 28, 2022

Related U.S. Application Data

(63) Continuation of application No. 16/050,418, filed on Jul. 31, 2018, now Pat. No. 11,170,662, which is a
(Continued)

(51) Int. Cl.
*G09B 19/00* (2006.01)
*G06N 5/02* (2023.01)
(Continued)

(52) U.S. Cl.
CPC ........... *G09B 19/0092* (2013.01); *G06N 5/02* (2013.01); *G09B 5/02* (2013.01); *G16H 20/60* (2018.01);
(Continued)

(58) Field of Classification Search
None
See application file for complete search history.

(56) References Cited

U.S. PATENT DOCUMENTS 4,147,514 A 4/1979 Magers et al.
4,844,867 A 7/1989 Bather
(Continued)

FOREIGN PATENT DOCUMENTS

EP 1 524 522 4/2005
WO WO 03/039367 5/2003
(Continued)

OTHER PUBLICATIONS

Ahmad, L. et al., "Design of a Breath Ketone Sensor for Obesity Management", Poster Presentation, Fall Meeting of the Biomedical Engineering Society, 2004, in 3 pages.
(Continued)

*Primary Examiner* — James B Hull
(74) *Attorney, Agent, or Firm* — Knobbe, Martens, Olson & Bear, LLP

(57) ABSTRACT

A system is disclosed that uses profiles of users, including monitored ketone levels of the users, to assess effectiveness levels of health programs (such as weight loss programs) assigned to the users, and to select health program modifications for the users. The system may use a machine learning (artificial intelligence) algorithm to adaptively learn how to classify users and to select messaging and behavioral modifications for the users. For example, in some embodiments the system classifies the users and provides associated health program recommendations using a computer model trained with expert-classified user data records. As another example, a set of rules may be used to generate the health program recommendations and related messaging, and the set of rules may automatically be modified over time based on feedback data reflective of health program effectiveness levels produced by such rules. In some embodiments the system includes a mobile application that runs on mobile devices of users and communicates wirelessly with breath analysis
(Continued)

devices of the users. The mobile application may also communicate with a server-based system that generates the health program recommendations.

21 Claims, 15 Drawing Sheets

Related U.S. Application Data continuation of application No. 15/588,414, filed on May 5, 2017, now Pat. No. 10,068,494.

(60) Provisional application No. 62/408,208, filed on Oct. 14, 2016.

(51) Int. Cl.

| | | |
|---|---|---|
| *G09B 5/02* | (2006.01) |
| *G16H 20/60* | (2018.01) |
| *G16H 20/70* | (2018.01) |
| *G16H 40/63* | (2018.01) |
| *G16H 50/70* | (2018.01) |
| *G06N 20/00* | (2019.01) |

(52) U.S. Cl.
CPC ............. *G16H 20/70* (2018.01); *G16H 40/63* (2018.01); *G16H 50/70* (2018.01); *G06N 20/00* (2019.01); *G09B 19/00* (2013.01)

(56) References Cited

U.S. PATENT DOCUMENTS

| | | | |
|---|---|---|---|
| 4,931,404 A | 6/1990 | Kundu |
| 4,970,172 A | 11/1990 | Kundu |
| 5,071,769 A | 12/1991 | Kundu et al. |
| 5,174,959 A | 12/1992 | Kundu et al. |
| 5,465,728 A | 11/1995 | Phillips |
| 5,834,626 A | 11/1998 | De Castro et al. |
| 6,010,459 A | 1/2000 | Silkoff et al. |
| 6,067,989 A | 5/2000 | Katzman |
| 6,190,858 B1 | 2/2001 | Persaud |
| 6,206,837 B1 | 3/2001 | Brugnoli |
| 6,221,026 B1 | 4/2001 | Phillips |
| 6,234,006 B1 | 5/2001 | Sunshine et al. |
| 6,254,547 B1 | 7/2001 | Phillips |
| 6,454,723 B1 | 9/2002 | Montagnino |
| 6,540,691 B1 | 4/2003 | Phillips |
| 6,582,376 B2 | 6/2003 | Baghdassarian |
| 6,599,253 B1 | 7/2003 | Baum et al. |
| 6,607,387 B2 | 8/2003 | Mault |
| 6,609,068 B2 | 8/2003 | Cranley et al. |
| 6,629,934 B2 | 10/2003 | Mault et al. |
| 6,658,915 B2 | 12/2003 | Sunshine et al. |
| 6,726,637 B2 | 4/2004 | Phillips |
| 6,841,391 B2 | 1/2005 | Lewis et al. |
| 6,981,947 B2 | 1/2006 | Melker |
| 7,052,854 B2 | 5/2006 | Melker et al. |
| 7,104,963 B2 | 9/2006 | Melker et al. |
| 7,220,387 B2 | 5/2007 | Flaherty et al. |
| 7,300,408 B2 | 11/2007 | Hancock et al. |
| 7,364,551 B2 | 4/2008 | Allen et al. |
| 7,533,558 B2 | 5/2009 | Flaherty et al. |
| 7,794,994 B2 | 9/2010 | Cranley et al. |
| 7,837,936 B1 | 11/2010 | Martin |
| 7,920,998 B2 | 4/2011 | Brown |
| 7,976,467 B2 | 7/2011 | Young et al. |
| 8,021,308 B2 | 9/2011 | Carlson et al. |
| 8,036,708 B2 | 10/2011 | Oozeki |
| 8,286,088 B2 | 10/2012 | Shaffer et al. |
| 8,287,454 B2 | 10/2012 | Wolpert et al. |
| 8,342,178 B2 | 1/2013 | Hengstenberg et al. |
| 8,399,837 B2 | 3/2013 | Robbins et al. |
| 8,514,086 B2 | 8/2013 | Harper et al. |
| 8,680,974 B2 | 3/2014 | Meiertoberens et al. |
| 8,816,862 B2 | 8/2014 | Harper et al. |
| 8,848,189 B2 | 9/2014 | Atkin et al. |
| 8,871,521 B2 | 10/2014 | Akers, Jr. |
| 8,917,184 B2 | 12/2014 | Smith et al. |
| 9,170,225 B2 | 10/2015 | Dutta et al. |
| 9,173,595 B2 | 11/2015 | Böhm et al. |
| 9,341,632 B1 | 5/2016 | Ahmad et al. |
| 9,486,169 B1 | 11/2016 | Ahmad |
| 10,068,494 B2 | 9/2018 | Ahmad et al. |
| 2003/0208133 A1 | 11/2003 | Mault |
| 2004/0018114 A1 | 1/2004 | Wang et al. |
| 2007/0245810 A1 | 10/2007 | Carter et al. |
| 2007/0258894 A1 | 11/2007 | Melker et al. |
| 2008/0008666 A1 | 1/2008 | Phillips |
| 2008/0053194 A1 | 3/2008 | Ahmad |
| 2008/0234553 A1 | 9/2008 | Urman et al. |
| 2009/0054799 A1 | 2/2009 | Vrtis et al. |
| 2010/0301197 A1 | 12/2010 | Boyle |
| 2011/0028091 A1 | 2/2011 | Higgins et al. |
| 2011/0098590 A1 | 4/2011 | Garbutt et al. |
| 2012/0071737 A1 | 3/2012 | Landini et al. |
| 2012/0130732 A1 | 5/2012 | Blander et al. |
| 2012/0295595 A1 | 11/2012 | Gibori et al. |
| 2013/0150746 A1 | 6/2013 | Tao et al. |
| 2013/0231711 A1 | 9/2013 | Kaib |
| 2013/0253358 A1 | 9/2013 | Phillips |
| 2014/0366610 A1 | 12/2014 | Rodriguez |
| 2015/0073233 A1 | 3/2015 | Rich et al. |
| 2015/0168307 A1 | 6/2015 | Kück et al. |
| 2015/0289782 A1 | 10/2015 | Peverall et al. |
| 2016/0081620 A1 | 3/2016 | Narayanan et al. |
| 2016/0146779 A1 | 5/2016 | Gallagher et al. |
| 2016/0150995 A1 | 6/2016 | Ratto et al. |
| 2016/0270724 A1 | 9/2016 | Ahmad et al. |
| 2017/0039336 A1 | 2/2017 | Bitran et al. |
| 2019/0096281 A1 | 3/2019 | Ahmad et al. |

FOREIGN PATENT DOCUMENTS

| | | |
|---|---|---|
| WO | WO 03/039483 | 5/2003 |
| WO | WO 2005/082234 | 9/2005 |
| WO | WO 2010/094967 | 8/2010 |
| WO | WO 2011/104567 | 9/2011 |
| WO | WO 2015/134390 | 9/2015 |

OTHER PUBLICATIONS

Barnett, D. et al., "Breath acetone and blood sugar measurements in diabetes", Clinical Science, vol. 37 (1969), in 1 page.

"CMS Operator Guide", CMS Operator Training 0108, dated Apr. 19, 2002, in 10 pages. URL: http://www.buydraegertubes.com/ds/cms-ops-guide.pdf.

Crofford, O. et al., "Acetone in Breath and Blood", Transactions of the American Clinical and Climatological Association, vol. 88 (1977), in 12 pages.

Diskin, A. et al., "Time variation of ammonia, acetone, isoprene and ethanol in breath: a quantitative SIFT-MS study over 30 days", Physiological Measurement, vol. 24 (2003), in 13 pages.

Dräger CMS Production Information (document properties of document indicate that the document was created on Dec. 1, 2008), in 4 pages. URL: http://www.draeger.com/sites/assets/PublishingImages/Products/cin_chip_measurement_system/US/cms-ds-pi-9044337-en-US.pdf.

DrägerTubes & Accuro Pump Production Information (document properties of document indicate that the document was created on Nov. 11, 2008), in 4 pages. URL: http://www.draeger.com/sites/assets/PublishingImages/Products/cin_accuro/US/081209-pi-DetectorTubes-22-10-2008-en.pdf.

Dubowski, K. et al., "Response of Breath-Alcohol Analyzers to Acetone: Further Studies", Journal of Analytical Toxicology, vol. 8, Sep./Oct. 1984, in 4 pages.

Gervais, T. et al., "Mass transport and surface reactions in microfluidic systems", Chemical Engineering Science, vol. 61 (2006), in 20 pages.

(56)                    References Cited

OTHER PUBLICATIONS

Ketonix US, "Ketonix 2015 Blue Specifications", 2015, in 2 pages. URL:https://www.ketonix.com/index.php/product-2/ketonix-2015-blue.

Ketonix, "Ketonix data for Michel Lundell", 2015, in 1 page. URL: https://www.ketonix.com.

Khan, A. et al. "Evaluation of a bedside blood ketone sensor: the effects of acidosis, hyperglycaemia and acetoacetate on sensor performance", Diabetic Medicine, vol. 21 (2004), in 5 pages.

Kundu, S. et al., "Breath Acetone Analyzer: Diagnostic Tool to Monitor Dietary Fat Loss", Clinical Chemistry, vol. 39 (1993), in 6 pages.

Kundu, S. K. et al., "Novel Solid-Phase Assay of Ketone Bodies in Urine", Clinical Chemistry, vol. 37 (1991), in 5 pages.

Kupari, M. et al., "Breath Acetone in Congestive Heart Failure", The American Journal of Cardiology, vol. 76, Nov. 15, 1995, in 3 pages.

Landini, B. et al., "Breath Acetone Concentration Measured Using a Palm-Size Enzymatic Sensor System", IEEE Sensors Journal, vol. 9, Dec. 2009, in 6 pages.

Landini, B. et al., "Effect of Exhalation Variables on the Current Response of an Enzymatic Breath Acetone Sensing Device", IEEE Sensors Journal, vol. 10, Jan. 2010, in 6 pages.

Likhodii, S. et al., "Breath Acetone as a Measure of Systemic Ketosis Assessed in a Rat Model of the Ketogenic Diet", Clinical Chemistry, vol. 48 (2002), in 6 pages.

Loken, S. C., "Breath Acetone and Ketone Metabolism in Obese and Diabetic Mice", Diabetes, vol. 25 (1976), in 1 page.

"Figaro Gas Sensor TGS 822", Figaro Engineering Inc., Mar. 1987, in 10 pages.

"MiniMed 530G System User Guide", Medtronic MiniMed, Inc., 2012, in 312 pages.

Musa-Veloso, K. et al., "Breath acetone is a reliable indicator of ketosis in adults consuming ketogenic meals", The American Journal of Clinical Nutrition, vol. 76 (2002), in 6 pages.

Schwarz, K. et al., "Breath acetone-aspects of normal physiology related to age and gender as determined in a PTR-MS study", Journal of Breath Research, vol. 3 (2009), in 9 pages.

Wang, L. et al., "Nanosensor Device for Breath Acetone Detection", Sensor Letters, vol. 8 (2010), in 4 pages.

Wang, L., "Tailored synthesis and characterization of selective metabolite-detecting nanoprobes for handheld breath analysis", Dissertation Ph. D. Thesis, Stony Brook University, Dec. 2008, in 127 pages.

Yoon, S. et al., "Active control of the depletion boundary layers in microfluidic electrochemical reactors", Lab on a Chip, vol. 6 (2006), in 9 pages.

User must stay at 20 g for
Personal Preference

App should provide help with
Add/subtract exercise
Difference food choices

Ketone Score = 4

7 Days

User must stay at 20 g for
Personal Preference

App should provide help with
Add/subtract exercise
Difference food choices

*But at careful time increments*

7 Days

Ketone Score = 4

User must stay at 20 g for
Until KS = 7. Exercise Caution.

App should provide help with
Can experiment but should
maintain KS of 2+

User must stay at 20 g for
Until all weight is lost

App should provide help with
Motivate to stick with 20g of carbs

Likely increase in rate of weight loss or "satisfactory" feelings.

Possibly easier to sustain without cravings.

USER 1

Goals: Weight loss without compromising workout

History: Has measured ketones before

Deviations from Time Window: 0 out of 21. 1 extra measurement.

Achieved KS >= 4: Day 3

Max Sustained Valued: KS = 12

Adjustment: Add 1/2 cup of rice, counter with increased exercise

| Date | Day 1 | Day 2 | Day 3 | Day 4 | Day 5 | Day 6 | Day 7 | Day 8 | Day 9 | Day 10 | Day 11 | Day 12 | Day 13 | Day 14 | Day 15 | Day 16 | Day 17 | Day 18 | Day 19 | Day 20 | Day 21 | Day 22 | Day 23 | Day 24 |
|------|-------|-------|-------|-------|-------|-------|-------|-------|-------|--------|--------|--------|--------|--------|--------|--------|--------|--------|--------|--------|--------|--------|--------|--------|
| KS | 2 | 1 | 4 | 5 | 3 | 5 | 6 | 4 | 9 | 9 | 11 | 9 | 11 | 12 | 12 | 11 | 11 | 11 | 12 | 12 | 12 | 11 | 11 | 10 |

*FIG. 4A*

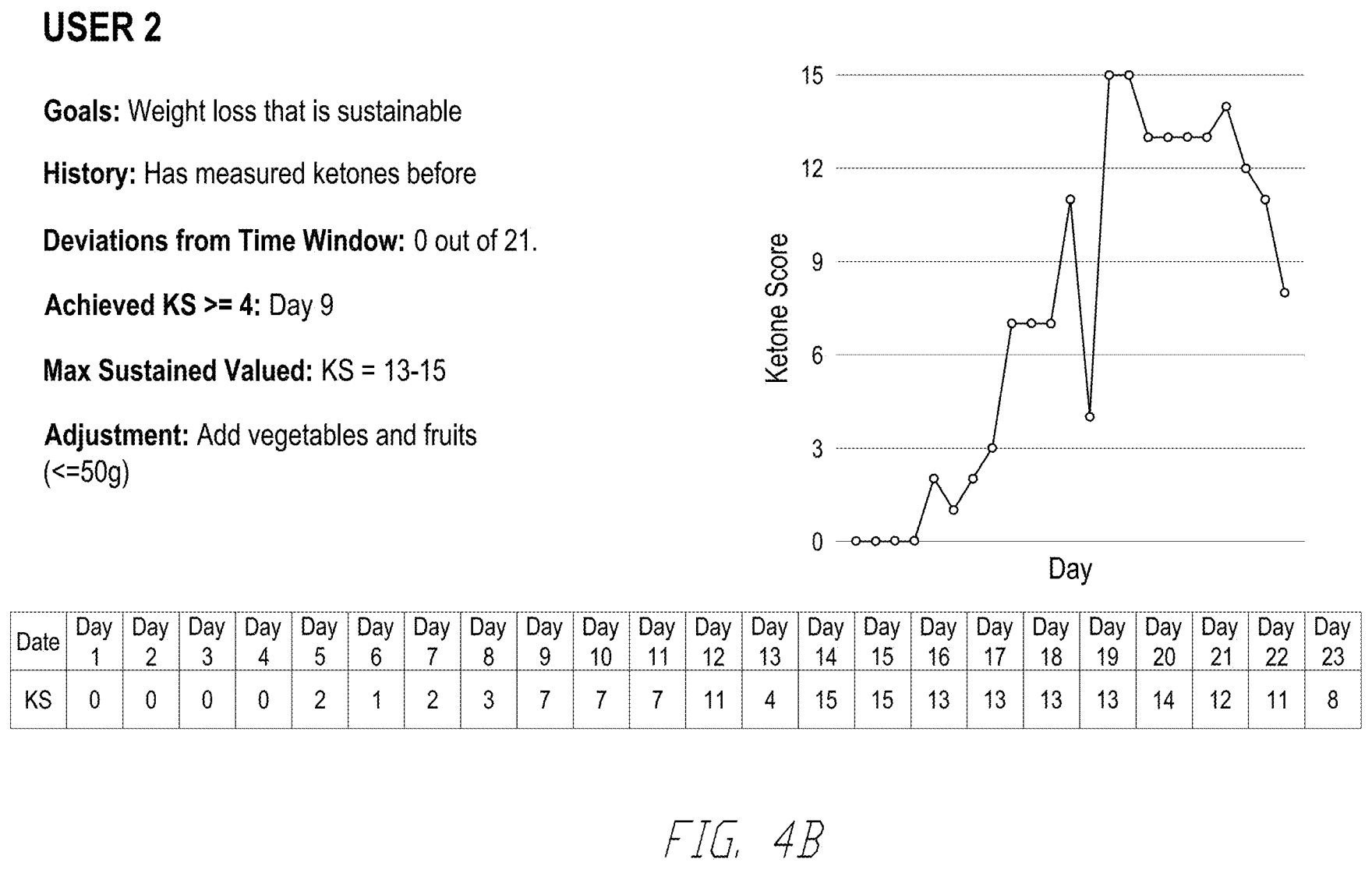

USER 2

Goals: Weight loss that is sustainable

History: Has measured ketones before

Deviations from Time Window: 0 out of 21.

Achieved KS >= 4: Day 9

Max Sustained Valued: KS = 13-15

Adjustment: Add vegetables and fruits (<=50g)

| Date | Day 1 | Day 2 | Day 3 | Day 4 | Day 5 | Day 6 | Day 7 | Day 8 | Day 9 | Day 10 | Day 11 | Day 12 | Day 13 | Day 14 | Day 15 | Day 16 | Day 17 | Day 18 | Day 19 | Day 20 | Day 21 | Day 22 | Day 23 |
|---|---|---|---|---|---|---|---|---|---|---|---|---|---|---|---|---|---|---|---|---|---|---|---|
| KS | 0 | 0 | 0 | 0 | 2 | 1 | 2 | 3 | 7 | 7 | 7 | 11 | 4 | 15 | 15 | 13 | 13 | 13 | 13 | 14 | 12 | 11 | 8 |

*FIG. 4B*

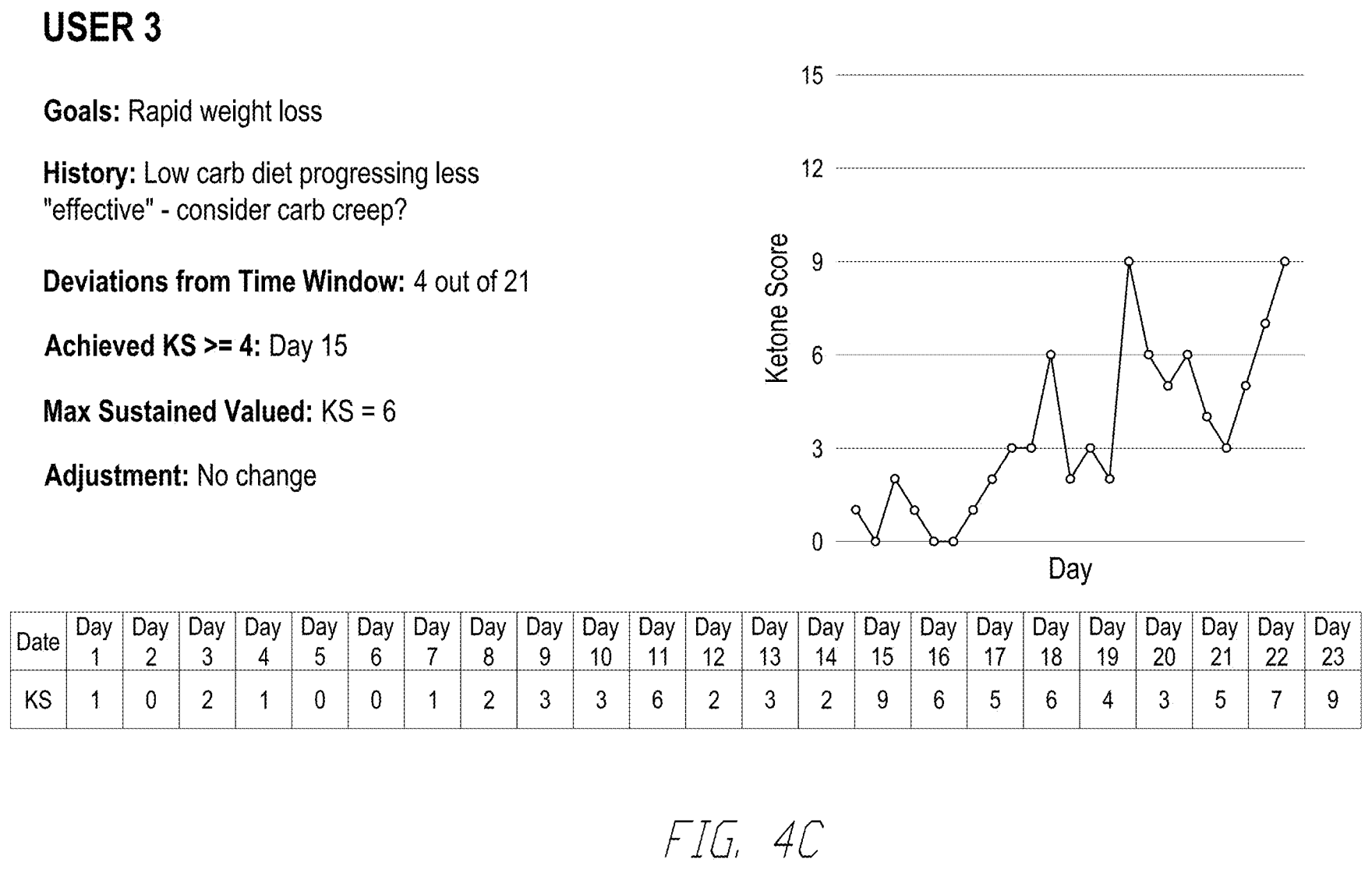

USER 3

Goals: Rapid weight loss

History: Low carb diet progressing less "effective" - consider carb creep?

Deviations from Time Window: 4 out of 21

Achieved KS >= 4: Day 15

Max Sustained Valued: KS = 6

Adjustment: No change

| Date | Day 1 | Day 2 | Day 3 | Day 4 | Day 5 | Day 6 | Day 7 | Day 8 | Day 9 | Day 10 | Day 11 | Day 12 | Day 13 | Day 14 | Day 15 | Day 16 | Day 17 | Day 18 | Day 19 | Day 20 | Day 21 | Day 22 | Day 23 |
|------|-------|-------|-------|-------|-------|-------|-------|-------|-------|--------|--------|--------|--------|--------|--------|--------|--------|--------|--------|--------|--------|--------|--------|
| KS | 1 | 0 | 2 | 1 | 0 | 0 | 1 | 2 | 3 | 3 | 6 | 2 | 3 | 2 | 9 | 6 | 5 | 6 | 4 | 3 | 5 | 7 | 9 |

*FIG. 4C*

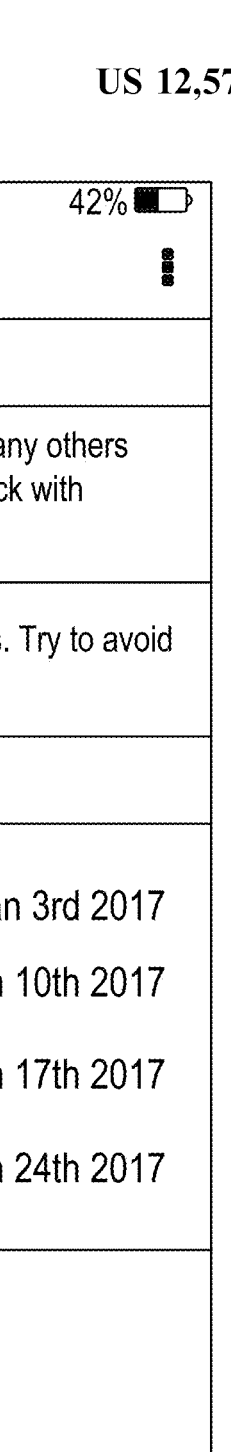

●●●○○Carrier 📶     9:41 AM     42% 🔋

Your Journey   ⋮

Insights about you...

You tend to take longer to lose weight than many others (20th percentile). Keep that mind and try to stick with healthy lifestyle choices.

You appear to have sensitivity to diet products. Try to avoid diet drinks.

Your journey so far...

⚡ Calibrating         Jan 3rd 2017

-5 lbs.         Jan 10th 2017

-2 lbs.         Jan 17th 2017

🗓 Today. 145 lbs.         Jan 24th 2017

Dashboard     Messages     Journey     Learn

FIG. 9

ARTIFICIAL INTELLIGENCE BASED HEALTH COACHING BASED ON BREATH ANALYTE LEVELS OF PARTICIPANTS

PRIORITY CLAIM

This application is a continuation of U.S. application Ser. No. 16/050,418, filed Jul. 31, 2018, which is a continuation of U.S. application Ser. No. 15/588,414, filed May 5, 2017 (now U.S. Pat. No. 10,068,494), which claims the benefit of U.S. Provisional Appl. No. 62/408,208, filed Oct. 14, 2016. The disclosures of the aforesaid applications are hereby incorporated by reference.

TECHNICAL FIELD

The present disclosure relates to machine-based processes, including machine learning processes, for automatically coaching participants in a weight loss or other health related program based on monitored ketone levels of the participants.

BACKGROUND

Obesity is a major individual and public health concern in the United States and throughout the world. In the United States alone, approximately 33% of the adult population is obese and another 33% are overweight. Treatment of obesity and other weight-related disorders involves a multi-factorial approach (typically a combination of diet, exercise, behavioral health modifications and sometimes medication or surgery) and commonly requires significant and sometimes permanent lifestyle modification. Especially in adults, the oft-required lifestyle changes can make obesity an extremely difficult condition to overcome.

The main goal of obesity management is reducing the amount of fat in the body. For various reasons (to motivate subjects, to enforce compliance and to troubleshoot/customize diets), it is useful and important to have a means to track and trend fat metabolism.

As an example, individuals suffering from other metabolic conditions, such as elevated cholesterol or high blood pressure, may benefit from improving their diet or changing exercise patterns. A growing number of individuals seek to reduce their carbohydrate intake to increase utilization of fat as an energy source, in hopes of reducing their overall insulin usage and thereby counteracting metabolic abnormalities (such as high blood pressure).

Athletes and fitness-conscious individuals are concerned about staying in peak physical condition, and are often actively engaged in structured sports activities (whether professional or not). Such individuals struggle with making data-driven decisions about how best to optimize their biochemical and physical condition. They often try to make "smart" decisions about how best to reach their fitness or health goals.

However, tracking and trending fat metabolism is useful beyond weight management and the treatment of obesity. Anorexia nervosa is a psychiatric disorder having substantial implications and is oftentimes a lifelong illness. The disorder is most prevalent in adolescents and young adults, and is 90% more common in young women than men. Because of the complex nature of the disorder and the significant level of mental health treatment, treatment of anorexia nervosa is most effective in-center and is correspondingly expensive. Improving patient outcomes requires considerable counseling and monitoring.

SUMMARY OF THE DISCLOSURE

A system is disclosed that uses profiles of users, including monitored ketone levels of the users, to assess effectiveness levels of health programs (such as weight loss programs) assigned to the users, and to select health program modifications for the users. The system may use a machine learning (artificial intelligence) algorithm to adaptively learn how to classify users and to select messaging and behavioral modifications for the users. For example, in some embodiments the system classifies the users and provides associated health program recommendations using a computer model trained with expert-classified user data records. As another example, a set of rules may be used to generate the health program recommendations and related messaging, and the set of rules may automatically be modified over time based on feedback data reflective of health program effectiveness levels produced by such rules. In some embodiments the system includes a mobile application that runs on mobile devices of users and communicates wirelessly with breath analysis devices of the users. The mobile application may also communicate with a server-based system that generates the health program recommendations.

BRIEF DESCRIPTION OF THE DRAWINGS

FIGS. 4A-4C illustrate the profiles, including ketone levels, of three individuals.

FIGS. 7-10 illustrate example screen displays of one embodiment of the mobile application.

DETAILED DESCRIPTION OF ILLUSTRATIVE EMBODIMENTS

Figure 1:
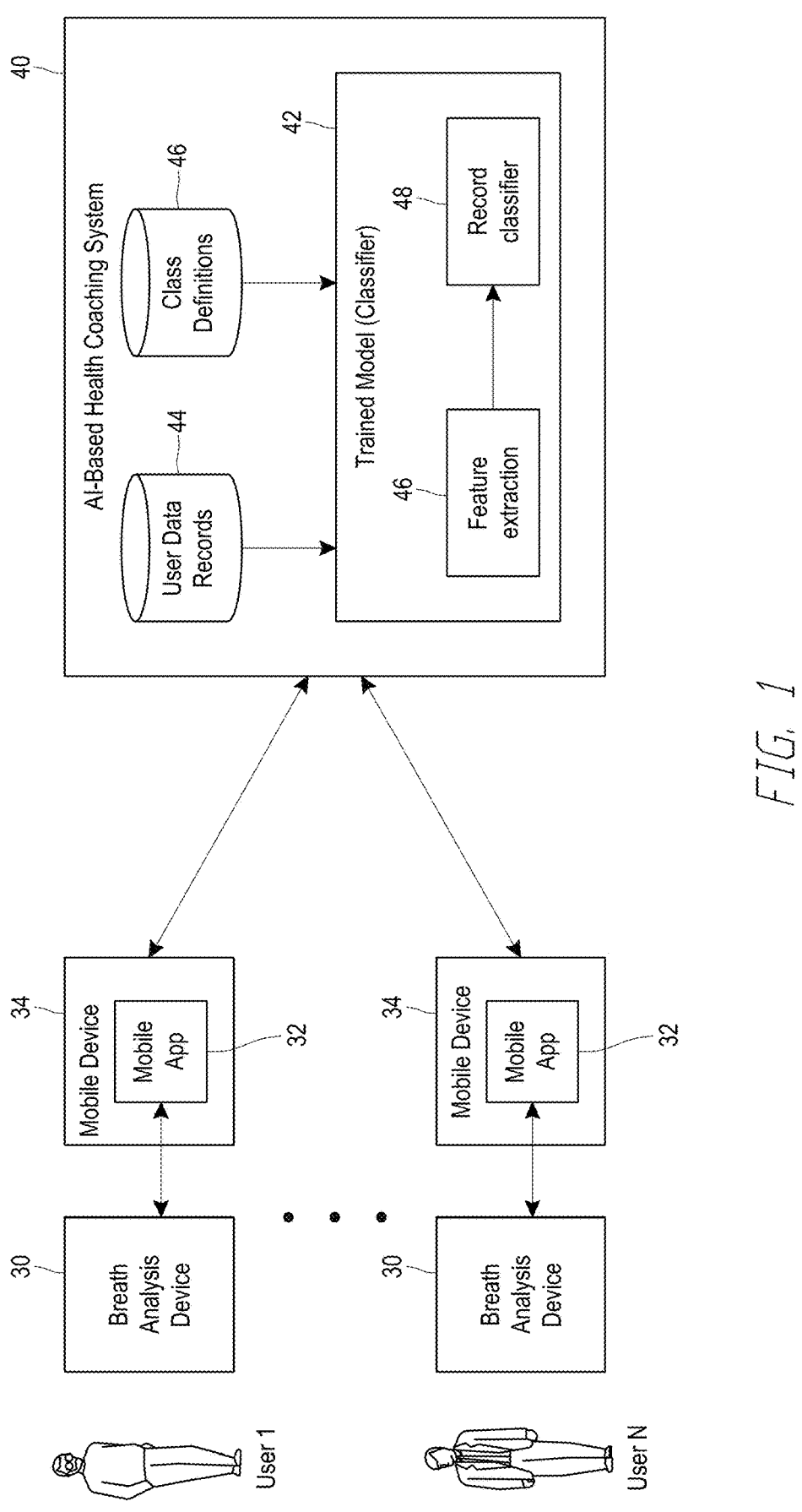
FIG. 1 illustrates an AI-based health coaching system according to one embodiment.

Ketones are useful to track and trend progress on a fat loss program and other health related programs. Ketone concentrations in the body and in body fluids (e.g., blood, urine, breath, or some combination of these) are correlated with fat metabolism. In the body, three main "ketone bodies" are generated: acetoacetic acid, $\beta$-hydroxybutyric acid, and acetone. In the case of acetone, because it is volatile, it is released into alveolar air when the blood brings it in contact with the lungs.

Generally, ketone levels increase in relation to increases in the body's fat metabolism. Higher ketone concentrations indicate greater metabolism of fat. During a net caloric deficit, greater fat metabolism portends increased loss of stored fat (e.g., a primary objective in weight reduction). Measurement of ketones offers the potential to be a powerful and accurate measure of fat metabolism, and therefore provides many advantages in the management of metabolic conditions and obesity management.

The term "ketone bodies" or "ketones" includes those that are present in the body including, without limitation, acetone, acetoacetic acid (also known as acetoacetate), and β-hydroxybutyric acid (also known as β-hydroxybutyrate or β-HBA). The devices and systems herein apply to measurement of ketones in breath, blood, urine, saliva, other body fluids, or via the skin.

Another instance in which measurement of breath acetone is useful is for the management and treatment of Type 1 diabetics. In Type 1 diabetics, where there is insufficient intracellular sugar or where sugar metabolism is impaired, the body resorts to metabolizing fat. This increase in fat metabolism can result in substantial and unwanted increases in ketone production. Because ketones are acidic, their build-up in the blood stream can cause a downward shift in blood pH, assuming that the body's ability to buffer pH is compromised or overwhelmed. This can result in a condition called diabetic ketoacidosis. In addressing this phenomenon, the objective is to monitor ketone levels to detect its onset and to aid in its management.

Portable breath analysis devices have recently become available that enable users to monitor their ketone levels. Examples of such devices are disclosed in U.S. Pat. No. 9,341,632 and U.S. Patent Appl. Nos. 62/338,312, filed May 18, 2016, Ser. No. 15/077,642, filed Mar. 22, 2016, 62/396, 240, filed on Sep. 19, 2016, and 62/368,311, filed Jul. 29, 2016, the disclosures of which are hereby incorporated by reference. In some cases, the portable breath analysis device uses a wireless (e.g., Bluetooth, WIFI, Zigbee) transceiver and connection to report the measurements to a mobile application that runs on the user's smartphone, tablet, or other mobile or personal device. The mobile application may in turn report the measurements to a remote system. In some cases, the breath analysis device may alternatively report the measurements to the remote system directly, in which case the mobile application may be omitted.

Given the availability of portable analysis devices (including breath analysis devices) with wireless capabilities, it is desirable to have a system that can provide automated, personalized feedback or coaching, such as weight loss coaching, to individual users based on their monitored ketone levels and other factors. FIG. 1 illustrates one embodiment of such a system. This system operates generally by monitoring ketone levels and other attributes of participants in health-related programs, and by making personalized, machine-generated changes or updates to such programs to improve program effectiveness. The programs may include or consist of diet and/or exercise programs intended to achieve weight loss or other health benefits. For purposes of illustration, the system will be described primarily in the context of weight loss programs, and the program participants will be referred to primarily as "users" of the system. The terms "recommendations," "program recommendations" and "coaching" will be used to refer generally to the auto-selected programs, program updates, behavioral modifications, and associated messaging, provided by the system to or for users.

As illustrated in FIG. 1, each user of the system uses a portable breath analysis device 30 generate ketone measurements from breath samples as described above and in the aforementioned patent references. Each such device 30 includes a ketone sensor capable of generating ketone measurements from breath samples of a corresponding user, and includes a wireless transceiver that is used to report the ketone measurements. The measured ketones may include, for example, acetone, acetoacetate, and/or B-hydroxybutyric acid. In some embodiments the ketone measurements may instead be generated from other types of bodily fluid samples of the users, such as blood or urine samples.

As the ketone measurements are generated, they are communicated over a communications network, which may include the Internet, to a remote, Artificial Intelligence (AI) based health coaching system 40. In the illustrated embodiment, each breath analysis device 30 communicates wirelessly with a mobile application ("mobile app") installed on a smartphone, tablet, or other mobile communications device ("mobile device") 34 of the respective user. The mobile application 34 may implement a variety of features (such as the features described in U.S. Pat. No. 9,341,632, which is hereby incorporated by reference herein) for assisting users in generating, monitoring and tagging ketone measurements, and for processing such measurements. In some embodiments, the breath analysis devices 30 may alternatively communicate directly with the health coaching system 40, such as via a WIFI connection; in these embodiments, the mobile application 32 and mobile device 34, may be omitted.

In some embodiments, the mobile application 32 may periodically ask the user various questions (e.g., "are you hungry?") to assess the effectiveness of the current program, and may record the user's answers. Further, the mobile application 32 may include a "daily journal" or "weekly questionnaire" feature through which the users can record various types of information and events. For example, users may specify that they are low on energy, hungry, constipated, or unhappy, or that they have deviated from their diet. In one embodiment the mobile application prompts the user to assign a numerical rating to each of the following: (1) energy level, (2) focus, (3) hunger, (4) good sleep, (5) pain, (6) constipation, (7) cravings, and (8) boredom.

The mobile application 32 may report these and other types of user information to the system 40 for use in providing personalized, machine-automated coaching. Further, in some embodiments the coaching may be supplemented or filtered by a human coach, in which case updates from the human coach may be recorded by the system and, in some cases, used by machine learning algorithms to improve the system.

In some embodiments, the system 40 may also be able to acquire other types of data about the users. For example, some users may use wireless glucose monitors that report glucose measurements to the health coaching system 40 via the mobile application 32 or via another channel. As another example, in the context of a weight loss program, the users/participants may use wireless scales that report their weight measurements to the system 40 via the mobile application 32 or otherwise. In one embodiment, the wireless scale, upon taking a weight measurement, wirelessly transmits the weight measurement to the mobile application 32 without displaying the measurement, such that it is withheld from the user; the wireless scale in this embodiment may lack a display.

As another example in the context of weight loss programs, the mobile application 32, or a separate mobile application (such as the MYFITNESSPAL™ application or LOSE IT™ application), may enable each user to track, and report to the system 40, their food intake and exercise activities. Other possible data sources include blood test results, heart rate data, location data (reflecting of visits to restaurants or gyms), credit card transaction logs (reflective of restaurant visits), sleep logs, the user's home address (reflective of what types of exercise the user may comfortably take part in because of weather patterns), and web search logs (reflective of user being hungry). Further, personal profiles (which may be stored as, for example, database records or text files) may be created by the system by the users themselves and/or their coaches, and may be considered by the system in providing coaching. These personal profiles may, for example, include demographic data (age, gender, ethnicity, etc.), weight loss (or other health-related) goals, genetic testing results, medical history data, and various other types of information.

As described below, the health coaching system 40 may use the above and other types of user/participant data to generate personalized recommendations and programs for the participants. In some cases, the coaching may be interactive in the sense that the system enables the user (or a health or weight loss coach of the user) to select from multiple options for attaining a desired goal. For example, a user may opt to want to lose weight as quickly as possible instead of a less aggressive strategy. Additionally, a user may indicate to the system 40 certain personal preferences, idiosyncrasies, and desired activities that the system 40 may take into account. For example, the user may indicate that they regularly go to the gym and lift heavy weights, that they bike to work, or that they really like or dislike certain types of foods. The recommendations may also be based on the current location of the user (as detected by the mobile device using a GPS receiver or other location-detection technology), and the proximity of that location to restaurants, gyms, the user's house, etc.

For purposes of illustration, the system 40 will be described primarily in the context of a weight loss program. As will be recognized, however, the underlying processes are also applicable to automated health coaching involving other types of conditions (such as diabetes and anorexia). For example, the system may support the ability for the user to select from the following types of goals: (1) lose weight, (2) gain weight, (3) enhance athletic performance, (4) treat or reduce the severity of some other medical condition, (5) learn more about how the participant's body reacts to various foods.

As further shown in FIG. 1, the health coaching system 40, in one embodiment, includes a trained model 42 that classifies users based on their ketone measurements and/or other user data. The trained model 42 classifies the users based on their data records 44 and a database of user class definitions 46. Each user data record may include, for example, a timestamped history of the user's ketone measurements (and any other measurements such as weight, glucose level, heart rate, etc.); demographic data such as age, gender, and height, and other user-supplied data such as medications taken; a timestamped history of the classifications and weight loss (or other health) programs assigned to the user, including program updates and recommendations generated by the system; weight loss goals; lifestyle habits; personal preferences; food intake events; exercise events; diet non-compliance events; user feedback on program satisfaction; nutritional sophistication level; etc. For some types of data, the users may provide the data to the system 40 by entering it into the mobile application 32, a web-based portal, or other data collection interface. Although the use of a trained model 42 is preferred, in some embodiments the system 40 may classify users, or otherwise make program recommendations, without the use of a trained model. For example, as described below with reference to FIG. 6, the system 40 may generate program recommendations using a collaborative filtering algorithm that seeks to recommend to a target user programs that have been effective for similar users.

A given user may be assigned to multiple classes concurrently, and the task of classifying a given user may, in some embodiments, be repeated whenever a new ketone measurement (or other significant data point) becomes available. Because a user's classification may change over time, the trained model 42 may assign classes as a function of other external parameters that exist outside of the user's data record. For example, the model 42 may be a function of the user's data record and a "target date" and the classes, 46, returned by the model, 42, may be interpreted as the classification of that user at the particular date. In one embodiment, some classifications assigned by the classifier 48 are of the user (or user data record) generally, and other classifications are of the effectiveness of a given program assigned to the user. An example of the later type of classification is an "effective" classification, which indicates that the health program assigned to the user is producing desired results.

In some embodiments, the classifier 48 may use a set of rules to classify users and to select actions to be performed. Some rules may, for example, be triggered by the receipt of a submission from a user's mobile device 32 of a ketone score, or other data point, that can potentially effect the user's current classification. An example of such a rule is one that determines whether the user's recent ketone scores justify a new categorization. Other rules may, for example be triggered by the reclassification of a user. For example, when a user is reclassified (such as from "effective" to "noncompliant"), a rule may be invoked that selects a new diet/exercise program for the user or that notifies a coach for the user. Other rules may, for example, be invoked periodically (e.g., once per week) based on the passage of time. A preferred embodiment of a rule-based implementation of the system is discussed below with reference to FIG. 5.

The class definitions 46 are selected or generated such that the class or classes to which a user is currently assigned map to particular recommendations (e.g. "reduce daily carb intake by X") and/or coaching protocols. These recommendations may be provided to the user by the mobile application 32, by a web portal, via text messages, and/or by any other communication method. The class-based recommendations may be generated by the health coaching system 40, the mobile application 32, or a combination thereof. Some classes may be defined manually by physicians and other experts, while others may be generated or inferred automatically using machine learning methods. Examples of classes (labeled in terms of their recommendations or coaching protocols) are:

No Change
Further decrease carbs
Increase fat
See a physician for a blood workup and medication assessment
Decrease protein
Remove artificial sweeteners
Initiate a fat fast.

As one example of how machine learning may be used, a group of experts may initially classify a number of user records into a set of classifications that correspond to respective coaching protocols or recommendations. For example, a human expert may review the record (including ketone measurements, weight loss goals, demographic data, etc.) of a weight loss program participant and make a recommendation (representing an assigned class) regarding an action to take or protocol to follow. These expert-classified records may then be used to train the model 42 using an appropriate algorithm, such as a Neural Network, Support Vector Machine (SVM), Probabilistic Graphical Model (including Bayesian networks or Markov models), or Decision Tree model. Through a training process, various user attributes or "features" are computed from the user's data records and then the algorithm learns how much weight to give to each feature by analyzing the classifications given by human experts to existing user records. These learned weights become an integral component of a trained model 42, and are used to reproduce the behavior of human experts on unseen user records. Examples of features that can be used are listed in Table 1. As described below, the system 40 may also adaptively adjust the weights over time based on the results, including weight loss results, produced by the system's classifications and associated recommendations.

TABLE 1

Example features

User-specified weight loss goal
BMI (computed from height and weight)
Age (computed from date of birth)
Sex
Average carbs for past 3 days (taken from diet log)
Average protein for past 3 days
Average fat for past 3 days
Average calories for past 3 days
Ketone (breath, blood or urine) reading at day t-0
Ketone (breath, blood or urine) reading at day t-1
Ketone (breath, blood or urine) reading at day t-2
Average heart rate for past 3 days
Medications
Ketone levels over first seven days after reducing daily carb intake to 20 grams
Evidence of insulin resistance from blood results or user's medications
Number of times user reported being hungry in last 7 days
Nutritional sophistication level The foregoing features are merely examples. In some embodiments the number of features may, for example, be in the hundreds. The system 40 may use a data repository of feature definitions to calculate or otherwise determine features for a user based on the user's data record.

As shown in FIG. 1, the trained model 42 includes a feature extractor 46 that computes, extracts, or generates the features based on a user record and other parameters, for example a "target date." These features are then passed to a record classifier 48 that assigns the user record to one or more of the defined classes. The record classifier 48 may include sub-classifiers as is known in the art. The set of one or more classes is then used to select corresponding messaging, and/or a coaching protocol, to be used for automatically coaching the respective user. Although a user's data record may be large, not all of the data in the record is necessarily considered during classification. For example, through feature extraction, the system may effectively disregard measurements taken, e.g., more than two weeks ago.

In some cases multiple distinct trained models may be used, such that the classification task is multilayered and nested. For example, some features may be used by one model to initially classify a user, and the results may be exposed as a feature to a "top-level" recommendations model. As another example, the system 40 may include different classifiers for different types of recommendations—for example, the system could include an "increase carbs" classifier and an "increase exercise" classifier, both of which operate as "yes or no" classifiers. As another example, the system could train and use separate models for males versus females, or for other demographic categories.

In some embodiments, the system 40 may include a supervised feedback loop in which computer-generated classifications are shown to human experts. The human experts can then indicate whether or not the trained model did the right thing. This data can be used by an iterative "training process" to continually improve the quality of the trained model in an on-line system. The system 40 could, for example, randomly ask an expert whether a prediction was correct.

The system could also assess the accuracy of its predictions without involving experts. For example, once the system classifies a user and provides a corresponding program recommendation, the system could track the user's progress over time, and could infer that the prediction/classification was inaccurate if the user fails to make progress (e.g., fails to lose weight).

In some embodiments, the system 40 may also use a machine learning process to automatically modify the class definitions, including the associated coaching recommendations, based on feedback. The feedback may include weight loss measurements reflective of the effectiveness levels of specific classifications and coaching protocols. Through this process, the system may learn, for example, that users whose ketone levels increase relatively slowly in response to carb reduction should be placed on a relatively strict carb reduction program for an extended time period.

In some embodiments the system 40 may assign a single class to a user record and associated parameters. In other embodiments, the system 40 may assign multiple classes. Some of these classes may map directly to recommendations while others may map to suggested options. For example, the system may classify a user and provide the recommendation that "no change is needed" while also providing the suggestion that they may "feel free to incorporate fruit in the diet."

Some of the defined classes may be persistent classes that are assigned permanently or for relatively long time periods. One example is the user/participant's nutritional sophistication level, which may be determined by having the user take an online survey. For relatively sophisticated users, the system may generate recommendations/messaging that includes more scientific terminology that for other users. For users with relatively low levels of nutritional sophistication, the system's output may include more pictures and less scientific terminology.

Another example of a persistent class is one that represents the rate at which a user's ketone score (representing a ketone level) increases to a desired level in response to a transition to a low-carb diet. This classification may be assigned by instructing the participant (e.g., via the mobile application 32) to reduce daily carb intake to, e.g., less than 20 grams, and to take daily ketone measurements during a particular time window each day. Based on the daily ketone measurements for a particular duration of time, the model 42 may then classify the user into one of N (e.g., 3, 4 or 5) classes, each corresponding to a different rate of increase. One such class may, for example, represent those users whose ketone score exceeds a desired threshold in less than seven days; for these users, the system 40 may select a protocol that gives the user a relatively high degree of flexibility in selecting dieting options. At the other end of the spectrum, a class may represent those users who are unable to reach the desired ketone score within 10 days; for these users, the system 40 may select a relatively strict protocol that, for example, requires the user to maintain daily carb intake at less than 20 grams (among other possible actions) until the desired weight loss is achieved. In some embodiments, the system 40 may use a fixed set of classes to classify the users, selected by human experts and the operators of the system 40. In other embodiments, the system 40 may learn the set of classes dynamically using machine learning (artificial intelligence) methods, for example K-Means clustering to identify groups of similar users that should be following similar protocols.

FIGS. 2A-2D illustrate an example of a set of four classes that may be used in this process. These figures all exemplify a two-variable system involving a pre-determined ketone threshold ("Ketone Threshold") and a time period ("System Time"). The Ketone Threshold is set based on the type of diet, the user's goals and, preferably but optionally, the values of others. In the following examples, the Threshold is set based on a low carbohydrate diet, where a level of 4 ppm (in the case of breath acetone) is above the population "baseline" breath acetone level and generally indicates a dieting/fat burning state. (The ketone score used in the examples represents parts per million of breath acetone.) The System Time is set based on the expected time that a user will reach the Ketone Threshold. In this example, the time is based on the amount of time that it takes an individual who understands carbohydrate restriction to see elevated ketones, not accounting for setbacks or metabolic challenges. Other values may be used.

Figure 2A:
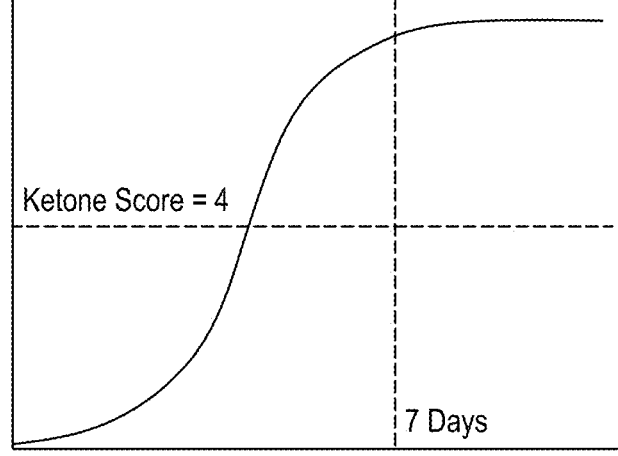
FIGS. 2A-2D illustrate examples of how ketone levels (scores) of users can be used to select health programs for the user.

The first, shown in FIG. 2A, represents users whose ketone score reaches 4 within the first seven days and stays well above that threshold. For these users, the system may provide coaching to the user on adding and subtracting exercise activities and modifying the user's diet. The diet modifications will typically allow the user to increase daily carb intake beyond 20 grams.

For example, the mobile application 32 may recommend foods that have a low glycemic index or are available at a restaurant that the user is visiting (e.g., "Your Ketone Score has been high over the past 5 days—nice job restricting your carbs. I see that you are going to Kona Grill, consider sharing a creme brûlée, which has fewer carbs and no starches. Stay away from the butter cake."). As another example, the mobile application may provide the following location-based messaging: "I see that you are at a sushi place. If you would like to have sushi tonight, have 3 pieces only. Then be sure to wear your heart rate monitor before leaving home tomorrow [remind user before the user leaves home]. Be sure to burn an extra 100 calories during your workout to compensate for the sushi that you ate [remind user during the workout]."

Figure 2B:
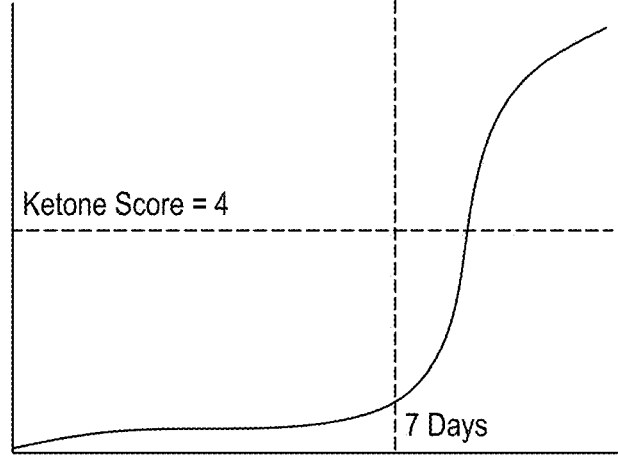

The second class, represented by the graph in FIG. 2B, represents users whose ketone score increases well above the threshold shortly after the seven-day threshold. For these users, the system may again give the user the option to exceed 20 grams of carbohydrates and to modify exercise; however, the system may regulate the timing of such changes so that the changes occur at controlled time increments.

Figure 2C:
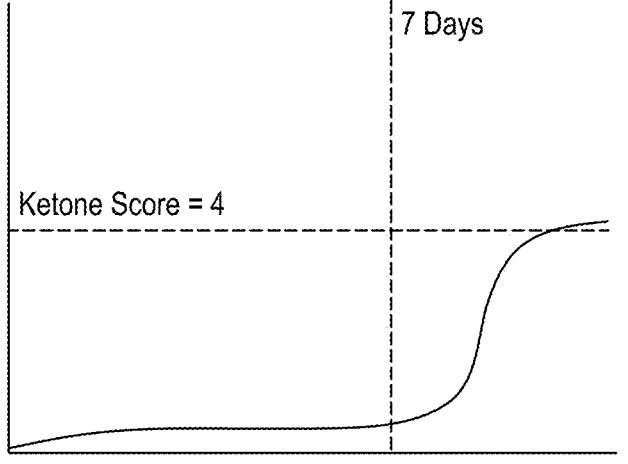

FIG. 2C illustrates a class in which the ketone score (KS) reaches the threshold of 4 after 7 days and thereafter remains slightly above that level. For these users, the system may instruct the user to keep daily carb intake below 20 grams until the ketone score (KS) reaches 7; the system thereafter enable the user to experiment with diet and/or exercise changes as long as the ketone score remains above 2.

Figure 2D:
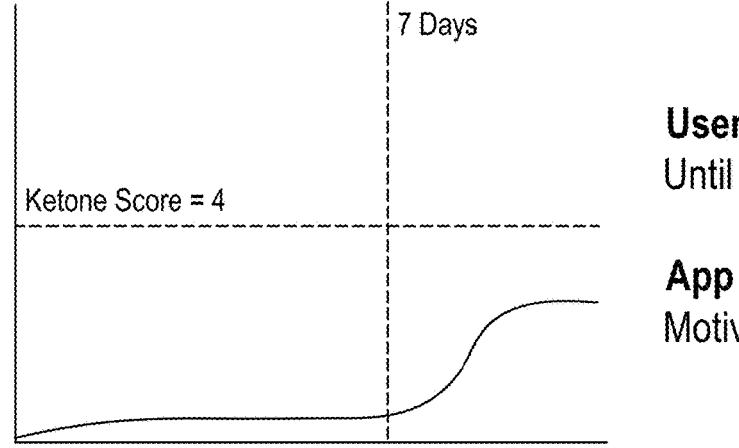

FIG. 2D represents a class in which the ketone score does not reach the threshold of 4 during the relevant time period. For these users, the system recommends that the user maintain daily carb intake below 20 grams, and may enter into a "troubleshooting" mode that seeks to learn the reason(s) why the ketone score is staying low. The troubleshooting protocol may, for example, instruct the user to reduce calorie intake, to take ketone measurements more frequently, to generate glucose measurements, and/or to take other actions useful for determining the reasons for the low ketone level increase. Examples of such actions include: further decreasing carbs, increasing fat intake, seeing a physician for a blood workup and medication assessment, decreasing protein, removing artificial sweeteners, and initiating a fat fast.

Figure 3:
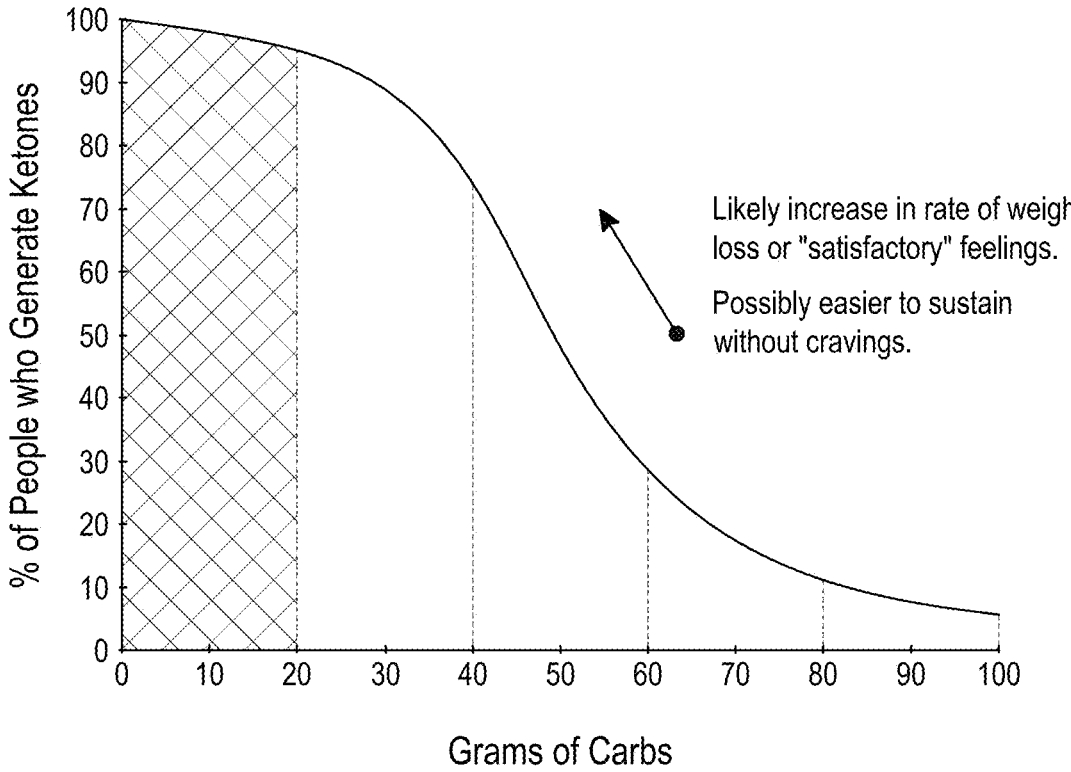
FIG. 3 illustrates the relationship between carbohydrate intake and ketone levels for a user population.

The graph shown in FIG. 3 illustrates why classes similar to those of FIGS. 2A-2D are useful. As this graph illustrates, most people will exhibit ketone levels above the population baseline (e.g., above 3 ppm in the case of breath acetone) if they reduce daily carb intake below 20 grams. As the graph shows, a significant portion of the population will also experience significant ketone level increases at higher levels of daily carb intake. Thus, it is desirable to identify, for specific users, the maximum carb intake level that will allow the user to reach a desired ketone level or range. For some users this level may be 20 grams, while for others it may be 30, 40 or higher. For these users with higher maximums, the system may enable the user to achieve their desired weight loss goals without severely restricting carb intake.

Ketosis is not a binary state. Even non-dieting, healthy individuals have ketones in their bloodstream, but at a low level. Thus, ketone levels are present in a spectrum. Although ketone levels are higher when an individual is on a low carbohydrate diet where the body is primarily using fat, an individual could generate ketones on a traditional "low calorie" diet where the body is using a mixed fuel tank (glucose and fat). Thus, a ketone monitor could be used to dial in to an individual's target level of carbohydrate restriction, but, for some individuals, could also help dial-in on a necessary level of calorie restriction. For example, Kundu et al. presented diets in which a patient group was consuming up to 147 g of carbohydrates, but on a 1200-calorie diet, and still generated ketones. In most circles, 147 g of carbohydrate consumption is not considered "low carb" but, for at least some individuals, such as those represented by the right-most portion of the graph above, they would expect to see some level of ketosis.

In one embodiment, when a user first begins using the system 40, the new user is instructed (e.g., by the mobile application 32) to start a low carb diet (e.g., below 20 grams of carbs per day), and the system initiates a "calibration" phase for the user to determine the rate at which the user's ketone levels change. This phase typically lasts for 10 to 14 days, during which the user in instructed to generate daily ketone measurements. At the end of the calibration phase, the classifier 48 uses the ketone scores to assign to the user a persistent classification (such as one of the four classifications shown in FIGS. 2A-2D) representing user's ketone level response to the low carb diet.

Following the calibration phase, the system 40 may periodically (e.g., on a daily basis, or when new measurement data is available) classify the user in terms of whether the user is burning or gaining fat. For example, as shown in the mobile application screen display of FIG. 7 (discussed below), the classifier 48 may assign to the user one of the following three classifications: Fat Storage, Neutral, or Fat Burn. The classifier may determine which of these three classifications applies based, for example, on (1) the user's ketone scores and weight measurements, (2) the user's ketone scores and resting heart rate, or (3) the user's ketone scores, weight measurements, and resting hear rate. Examples of algorithms (which may be implemented as rules) that may be used for this purpose are described below under the heading "Fat gain/loss classification."

In one embodiment, the task of classifying the user as being in a fat storage phase, neutral phase, or fat burn phase is performed once the user completes three daily tasks: (1) generating a ketone measurement with the breath analysis device 30, which reports the measurement to the mobile application 32 as described above, (2) generating a weight measurement (optionally with a wireless scale that reports the weight measurement to the mobile application 32 as described above), and (3) answering a set of questions that are presented by the mobile application 32. To remind the user to perform the first two tasks, both the scale and breath analysis device may light up in the morning (or at another appropriate time during the day) until they are used to take their respective measurements; the mobile application 32 may control the timing with which these devices light up. The mobile application 32 may also proactively present the user with the questions, or with a reminder to use the mobile application to answer the questions.

The profiles of three actual users will now be described with reference to FIGS. 4A-4C to further illustrate the factors that may be considered by the system 40 in coaching users. FIG. 4A illustrates a user having a weight loss goal of achieving "weight loss without compromising workout." The user's ketone measurements over a 24-day period are shown at the bottom of the figure. In this example, the ketone score exceeded four at day 3 after starting the low-carb (20 grams of carbs or less per day) diet, and remained well above that threshold thereafter. Based on this data and the classifications of FIGS. 2A-2D, the system would use the classification of FIG. 2A, allowing the user to vary his or her diet.

In this particular example, after day 20 the user was allowed an additional ½ cup of rice countered with increased exercise. This resulted in a small drop in the ketone score. In some cases the system 40 may respond to such a drop by recommending that the user take a particular action, such as initiating glucose monitoring to provide an additional indicator.

FIG. 4B shows the profile of a user having the goal of "weight loss that is sustainable." This user's ketone score did not exceed four until day 9, but exceeded this threshold by a significant margin thereafter. The class shown above in FIG. 2B corresponds to this user. After day 20 the user was permitted to add vegetables and fruit to the diet, resulting in a drop in the ketone score.

FIG. 4C shows the profile of a user having the goal of "rapid weight loss." This user's ketone score did not reach four until day 15, and only reached a maximum level of six. As a result, the user was instructed to not to make any diet changes, and to keep daily carb intake at or below 20 grams. Because this particular user deviated from the ketone measurement time window four times over 21 days, the system may assume, in generating recommendations, that the user has also likely deviated from the dietary restrictions.

Table 2 below shows another method that may be used by the system 40 to classify users for coaching purposes. In this example, each user is classified into one of four categories based on the user's weight loss goal or history. If the user's goal is to lose 50+ pounds or has a history of being 50+ pounds overweight, the system recommends that the user maintain daily carb intake at 20 grams or less until the weight loss goal is reached. For lesser weight loss goals, the amount of time for maintaining carb intake at or below 20 grams is progressively less, and the system 40 may implement a protocol for finding the optimal carb intake level or range. If a user in the lower three categories chooses to keep max daily carb intake to 20 grams, the system may compute, and notify the user of, an estimated time for reaching their desired weight loss goal.

TABLE 2

| Profile Method | Approach | |
|---|---|---|
| 50 + lbs.* | 20 g until weight is lost | Cannot toggle |
| 30 to 50 lbs. | 20 g for 6 months | Find optimal range, time not specified |
| 15 to 30 lbs. | 20 g for 3 months | Find optimal range, time not specified |
| <15 lbs. | 20 g for 6 weeks | Find optimal range, time not specified |

*or has a history of being 50 lbs. or more overweight

Other profile characteristics may include the user's medication history, prior "ketone" history, weight history, and general medical history. For example, if the user exhibits evidence of insulin resistance, this may be cause to profile the user into a separate category.

The example classifications illustrated in FIGS. 2A-2D and Table 2 are relatively simple classifications that look at only one user attribute or a small number of attributes. The system of FIG. 1 is capable of generating class definitions that rely on a much larger set of user attributes and features to classify users and user records. For example, once a set of users has been classified by a set of experts as "capable of significant weight loss at daily max carb intake of 40 grams and minimal exercise increase," the training algorithm may identify a relatively large number of user attributes and associated features (e.g., 10 or more) useful for automatically identifying these users. Once these users are identified by the trained model 42, the system may coach these users according to a protocol that only requires them to reduce daily carb intake to 40 grams and that does not require significant exercise increases.

The system 40 may also use regression to identify or modify cut-off values used for classification. Examples of such cut-off values are the ketone score threshold of 4, and the time period of seven days, used in the categories of FIGS. 2A-2D.

Referring again to FIG. 1, the health coaching system 40, including its illustrated components 42, 44, 46, 48 (and the additional components shown in FIG. 5, discussed below), may be implemented by a computer system programmed with executable program modules stored on one or more computer-readable media (hard disk drives, solid state memory devices, etc.). The coaching system 40 may be distributed or replicated across multiple physical servers or other computing devices of the computer system, which may or may not be co-located. Each such server typically includes one or more hardware processors that execute program instructions, a solid state memory, a network interface, and various other hardware components. The computer system may, in some embodiments, be a cloud computing system in which tasks are allocated dynamically to machines. The functionality of the coaching system 40 may be distributed among software components differently than shown in FIG. 1, and some components and functions may be omitted in some embodiments. The data repositories 44, 46 shown in FIG. 1 may include databases, flat file systems, and/or other types of data storage systems, and may use hard disk drives, solid state memories, and/or other types of non-transitory computer storage devices.

Further, the disclosed logic for classifying users and generating recommendations may, in some embodiments, be implemented partly or wholly in the mobile application 32. As one example, the coaching system 40 may push to the mobile application 32 the class definitions and other data needed to classify users and output associated recommendations, and the mobile application 32 may then use this information to coach the user.

The mobile devices 34 may include smartphones, tablet computing devices, smart watches, computerized eyewear devices, and other types of portable wireless devices capable of running applications. The mobile application 32 may be implemented in executable program code that is stored in the non-transitory computer storage (e.g., solid state memories) of the mobile devices 34. All of the processes and process steps described above may be embodied in, and fully automated via, the program components described above. Some or all of the functions may instead be performed by specialized computer hardware, such as ASICs or FPGA devices.

Figure 5:
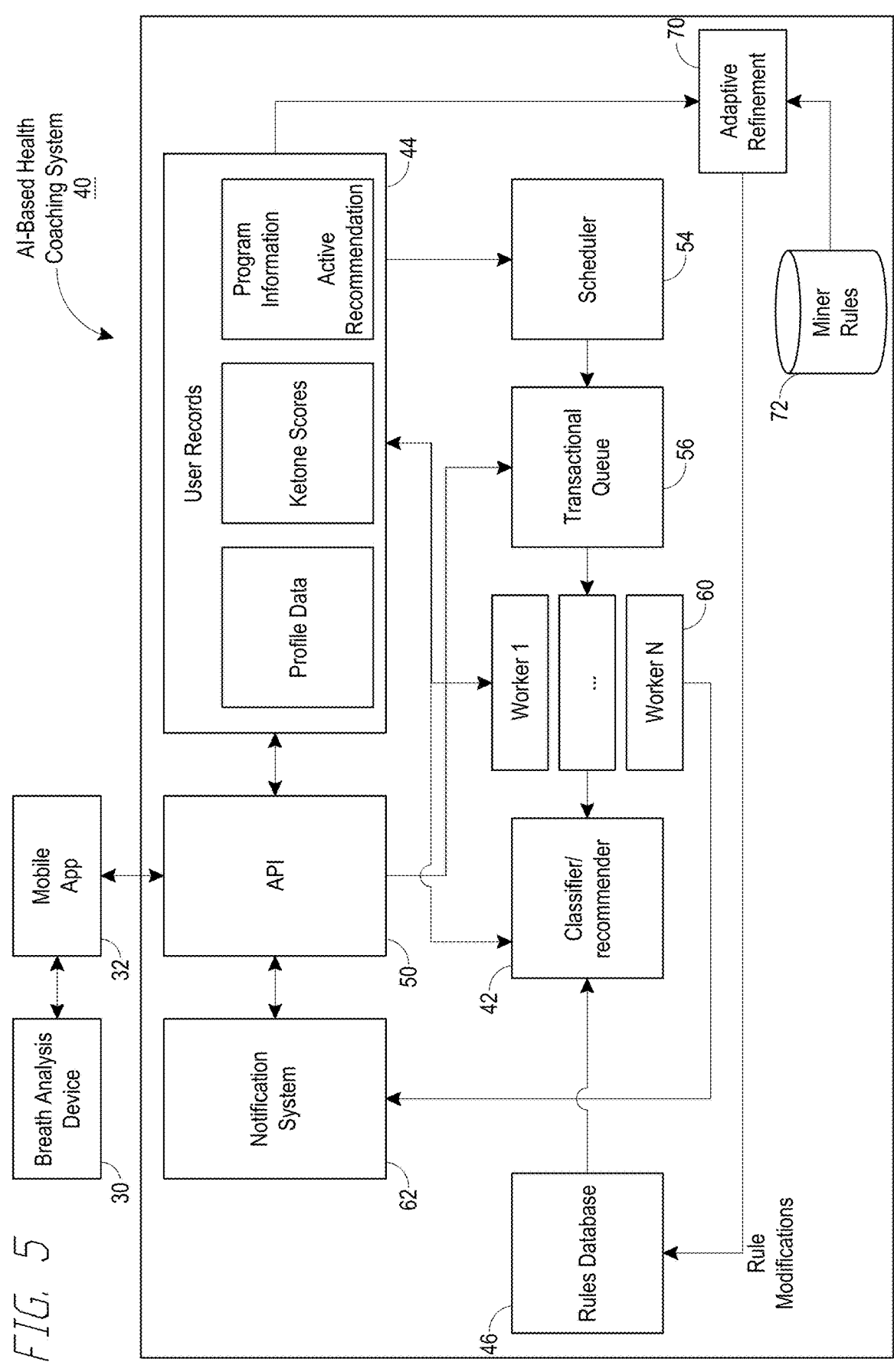
FIG. 5 illustrates a computer architecture that may be used to implement the system of FIG. 1.

FIG. 5 illustrates one embodiment of a system architecture that may be used to implement the AI-based health coaching system 40 of FIG. 1. In this embodiment, the mobile application 32 (one instance shown) communicates over a network with the system 40 via an API (Application Program Interface) 50, which may be exposed over HTTP. The API defines a series of endpoints that the mobile application 32 can call to invoke a procedure (such as initiating a classification update) or access or manipulate a remote resource. One notable resource that the mobile application 32 interacts with through the API is the set of user records 44. The user record for a given user typically contains the user's profile data (described above), ketone scores, and information about what health management (e.g., weight loss) program is currently assigned to the user. When the mobile application 32 gets new ketone scores from the breath analysis device 30, the mobile application reports the scores via the API, which stores them in the user records 44 in association with the user.

The system 40 may initiate reclassification of the user (and thus assessment of the current program's effectiveness) periodically or in response to a request/submission from the user's mobile application 32. With the periodic approach, a scheduler 54 periodically (e.g., once per day or once per week) places a classification task onto a transactional queue 56 for the user. The scheduler may always place a task on the queue or it may only do so if certain conditions are met (e.g., new ketone scores have been posted since the last time the user was classified).

With the request-based approach, the API 50 adds the classification task to the transactional queue 56 in response to receiving a request/submission from the mobile application 32. For example, the API may initiate recalculation of the program's effectiveness every 3 ketone readings it receives for the user; or, it may place a task on the transactional queue when an incoming request to the API indicates that the user has changed time zones (which indicates that the user may be traveling).

Worker machines 60 pull tasks from the queue 56 in a consistent and atomic manner such that, in a preferred embodiment, only one worker machine and process executes a task at a time and a task is executed a maximum of one time. The assigned worker machine executes the task and accesses data from the user's data record 44, and passes that information to the classifier/recommender 42. The classifier/recommender 42 analyzes the received data and optionally consults a rules database 46, which may contain class definitions and associated rules. Once the classifier/recommender 42 makes a classification, the assigned worker machine/process 60 can update the user's record and optionally send a notification to the user through a notification system 62. The notification system 62, if invoked, sends a message to the user's mobile application 32 to alert the user of new program information. This message preferably includes a value that informs the mobile application 32 that the program has changed and that it should re-fetch the user's program data from the API. The App may periodically "poll" the API at regular intervals to ensure that it gets up-to-date information on the program effectiveness even in the event that notification messages are lost or not reliably delivered. In some embodiments, the notification system 62 may instead proactively send the new program information to the user's mobile application 32.

As explained above, the messaging provided to the users may be tailored by the system to the nutritional sophistication levels of the users. Similarly, the system may tend to recommend more complex diets and/or exercise programs from relatively sophisticated users.

In some embodiments the results of the classification process may be a ranked list of health (e.g., weight loss) programs or program options. This ranked list may be presented directly to the user (e.g., via the mobile application, as described above), or may be presented to a health or weight loss coach of the user. In either case, if multiple options are presented, feedback from the user or coach may be solicited and recorded regarding which option is selected. In some cases a program recommendation/update generated by the system may be modified by the coach, in which case the coach may record the modification with the system. The program modifications entered by coaches may be used by system 40 to create new rules and/or modify existing rules.

In some implementations a human coach may be able to provide to the system 40 his or her input on a given recommendation after that recommendation has already been provided to the user/participant. For example, the system 40 may communicate a program update (e.g., "reduce daily carb intake by X") to the user, and may later solicit or otherwise obtain feedback from the user's coach on whether the update was helpful. This mode may be used for relatively low risk program participants, and for relatively minor program updates (e.g., minor diet or exercise changes).

In some embodiments the classifier/recommender 42 may be a non-rule driven subsystem, in which case the rules database 46 may be omitted. For example, the classifier (or a non-classifier type recommendation engine) could additionally or alternatively employ algorithms that incorporate Support Vector Machine (SVM), Hidden Markov Model (HMM), Collaborative Filtering, and other types of algorithms. As one example, the system may include a collaborative filtering based recommendation engine that maps users to similar users based on their respective user data records. The recommendation engine may then use these mappings to recommend to a given user a program or program option that has produced successful results (such as good ketone scores or weight loss results) for one or more similar users.

As shown in FIG. 5, the system may also include an adaptive refinement process 70 that monitors the ketone scores (and possibly other measures of success such as user satisfaction ratings and weight measurements) produced by specific rules and classifications, and which adjusts the rules database 46 accordingly. For example, the adaptive refinement process 70 may reduce or eliminate the system's reliance on a given rule (such as by modifying the rule's weight value) if that rule tends to produce poor ketone scores or low user satisfaction ratings.

As show in FIG. 5, the adaptive refinement process 70 may use a set of miner rules 72 to evaluate existing rules in the rules database 46. As one example, a miner rule may specify that "if a user does not lose weight within 15 days or receiving a program update, the program update is bad." Using this miner rule, the adaptive refinement process may search for updates (recommendations) that produced bad results, and may associate those negative outcomes with rule or rules used to generate the update. A miner rule may similarly be provided for searching for positive outcomes.) If, for example, the tally of positive outcomes is fails to exceed the tally of negative outcomes for a given rule, the rules database 46 may be updated to eliminate the rule or reduce reliance upon the rule.

The adaptive refinement process may also generate new rules. In embodiments in which the system records input from human coaches, the coach-supplied input may be used to generate or modify rules; for example, if coaches frequently make a particular modification to a particular recommendation generated by the system (such as by increasing an exercise duration recommendation from 20 to 30 minutes), the adaptive refinement process 70 may incorporate that modification into the rule used to generate that recommendation.

The system illustrated in FIG. 5 is designed to be scalable to accommodate large numbers of program participants (e.g., tens of thousands) and large quantities of data while providing good real time performance. For example, the number of worker machines may be increased as needed as the number of participants is increased. Each worker machine may include a processor and memory, and may execute a classification process as described above.

The various components of the system 40 in FIG. 5 may be hosted on a server-based computing system that comprises one or more physical servers or other computing devices, which may or may not be dedicated or persistently allocated to health-based coaching. The scheduler 54, transactional queue 56, classifier/recommender 42, API 50, notification system 62 and adaptive refinement component 70 may each be implemented in executable program code stored one or more persistent storage devices and executed by the computing system. In some embodiments the computing system may be geographically distributed, such that some devices of the system 40 are remote from other devices of the system 40. The various databases and data repositories 44, 46, 72 may be implemented using flat files, relational databases, and/or other types of data storage structures.

The recommendations provided by the classifier/recommender 42 are generally in the form of suggested behavioral modifications (e.g., "reduce carbs by X," or "increase workout time by Y"). These behavioral modifications are typically part of a new or modified health program selected for the user, but this need not be the case. For example, the system may recommend that the user take ketone measurements more frequently, or may recommend initiating glucose or heart rate testing. As discussed below, in some cases the recommendations may be in the form of a ranked list of programs (or other behavioral options) from which the user can make a selection.

In the embodiment of FIG. 5, the logic for classifying users and generating associated recommendations is implemented within the server-based system, remotely from the user devices. In some embodiment, this logic may alternatively be implemented partly or wholly within the mobile application 32. For example, the mobile application 32, as installed on a user device 34, may include a set of rules for classifying users and generating associated recommendations. These rules may be static, or may be updated over time by a server-based system. Thus, in some embodiments the tasks of classifying users and selecting coaching messages for such users may be performed by the mobile devices and mobile applications of the users without the involvement of a server.

The server-based computing system that hosts or implements the AI-Based coaching 40 system may also include components (not shown) for implementing other features, including features for analyzing and adjusting ketone measurements and for generating reminders and alerts. Examples of such features are described in U.S. Pat. Nos. 9,486,169 and 9,341,632, and U.S. Provisional Appl. No. 62/338,312, the disclosures of which are hereby incorporated by reference.

In addition to providing coaching to program participants (users), the system 40 may, in some embodiments, may provide automated coaching/recommendations to human coaches of such participants. For example, the system 40 may recommend to a human coach a particular coaching protocol for coaching a particular participant or class of participants.

User/Program Classification

Various implementation options for classifying users and generating associated program updates/recommendations will now be described.

In one embodiment, the inputs to the decision on how to classify the user (and/or the program to which the user is assigned) include some or all of the following information associated with the user: (1) ketone scores, (2) body weight measurements, (3) body composition reports, if available, (4) user history reports, and (5) user reported data, (6) number of missed ketone measurements (i.e., user fails to measure ketone level, (7) number of window aberrant ketone readings (i.e., user takes ketone measurement but outside the prescribed time window), (8) number of ketone measurements flagged by the user as being associated with non-program-compliant behavior. The possible classifications preferably include the following: (1) effective (i.e., the currently assigned program is effective for the user); (2) unhappy (e.g., the program is effective for weight loss but the user is bored, constipated, or otherwise dissatisfied); (3) adjusting (the program was effective but the user has adjusted and is getting diminished returns); (4) non-compliant (the user is not following the program, or is "cheating"); (5) ineffective (e.g., the program is not helping with fat burn and a change is needed). Numerous other classifications are possible.

In one embodiment, canonical curves are generated based on clinical data of ketone scores. These canonical curves represent different classifications. These curves may be scoped over a fixed period of time, such as two weeks from the start of the program. The system may classify a user based partly or wholly on how well the user's data matches one of the canonical curves. A rule may require a certain number of days' worth of data to be obtained before a classification is given.

Additionally, rules may be provided to look for salient signals and to circumvent regression comparisons. For example, if a user has missed more than 25% of their readings, a rule may automatically flag the user as non-compliant. As another example, a rule could be implemented that classifies a user as "unhappy" if the user reports that they are constipated more than 3 times over a 7 week period.

Other examples of rules include the following: (1) if a user's ketone score stays below 4 over X days, classify the user (program) as "ineffective," (2) if a user sometimes gets a ketone score over 4 but sometimes gets scores below 1, classify the user as "non-compliant," (3) if a user has slowly seen a monotonically decreasing trend in ketone scores for over a week, classify the user as "adjusting," (4) if rules (1)-(3) do not apply, classify the user/program as "effective," (5) if a user is classified as "effective," but repeatedly reports being constipated, being hungry, or having low energy, classify the user as "unhappy." The thresholds applied by these rules may be selected, or adjusted over time, using a regression process.

Additional classifications may be defined within the system 40 over time to better accommodate a wide range of variations between users. For example, a clustering algorithm may be applied to the user data records to search for new classifications. In one embodiment, the clustering algorithm generates 2×K clusters, where K is the current number of classifications, and generates a report that enables an administrator to assess whether any of the clusters should be converted into a new classification.

Each time a user is reclassified, the system 40 may take one of the following (among other) courses of action: (1) assign a new program to the user, (2) select a set of changes to the current program (e.g., adding a diet restriction), (3) output to the user a list of program options from which to make a selection, (4) suggest another type of behavioral modification, such as glucose testing, or (5) determine that no change is needed. The system may select between these courses of action using rules, using collaborative filtering (as described below with reference to FIG. 6), or using some other method.

Fat Gain/Loss Classification

As described above, the system in some embodiments periodically classifies each user as being in a Fat Burn phase (also referred to as "fat metabolism state"), a Fat Neutral phase, or a Fat Storage phase. As with the other types of classifications described herein, this classification task may be performed by either the server-based system (namely its classifier 48) or by the mobile application 32, and may be performed using a set of rules. As mentioned above, this classification task may be executed once the user completes the three daily tasks of measuring their weight, measuring their ketone level, and answering a set of questions.

The Fat Burn phase is based on elevated ketone levels and decreasing weight. If ketone levels are above a first user-specific threshold and weight is decreasing, the user is classified as being in the Fat Burn phase. If ketone levels are above a second user-specific threshold (lower than the first user-specific threshold) and weight is stable, the user is classified as being in the Fat Neutral phase. If ketone levels are below the second user-specific threshold or weight is increasing, the user is classifies as being in the Fat Storage phase. The ketone levels and weight are preferably averaged over a selected time period, such as a 7-day period, a 3-day period, or a 3-day period without any aberrant readings.

The system may also compute a Confidence Level for the classification. If, for example, the user is not performing any (or either) of the test steps each day or is not responding to the questions, the Confidence Level drops. If the user is seeing results that are outside the typical pattern (e.g., a ketone level that is 2 standard deviations above or below), the Confidence Level may drop.

To illustrate how users may be classified in terms of fat gain/loss (and coached accordingly), the data of five users is shown and discussed below. In these examples, the user is periodically asked to complete a "symptom card" that asks the user whether they are experiencing symptoms of hunger, constipation, lack of focus, lack of energy, lack of sleep, cravings, headaches, and diet fatigue (or boredom).

The data of a first user is shown in Table 3. The weight is trending downward, and the ketone scores are high (in this situation, $>=4$). This system would classify this user as being in the Fat Burn phase. Based on this determination and the lack of symptoms, the system would not recommend a diet change or other program change.

TABLE 3

| Day | Weight | Ketone Score | Symptom Card |
|---|---|---|---|
| 1 | 162.0 | 5 | No issues |
| 2 | 162.0 | 6 | — |
| 3 | 161.8 | 7 | — |
| 4 | 163.2 | 8 | — |
| 5 | 161.5 | 5 | — |
| 6 | 161.2 | 5 | — |
| 7 | 161.0 | 6 | — |
| 8 | 160.8 | 5 | — |
| 9 | 161.5 | 6 | — |
| 10 | 160.5 | 5 | — |

The data of a second user is shown in Table 4. Given the discrepancy between limited weight loss and high ketone scores, the system would preferably prompt this user to offer an explanation. For example, the system may ask the user to indicate whether there is unusually high salt intake (contributing to water retention), an increase in physical activity (contributing to possible muscle gain), constipation, bloating due to menstrual cycle initiation (if applicable), or other factors. This user is in a Fat Neutral Mode with, for example, an 80% confidence. If there is no change in another 5-6 days, the system may recommend a diet change.

TABLE 4

| Day | Weight | Ketone Score | Symptom Card |
|---|---|---|---|
| 1 | 162.0 | 5 | No issues |
| 2 | 162.0 | 6 | — |
| 3 | 161.8 | 7 | — |
| 4 | 163.2 | 8 | — |
| 5 | 162.0 | 5 | — |
| 6 | 161.5 | 5 | — |
| 7 | 162.3 | 6 | — |
| 8 | 162.0 | 5 | — |
| 9 | 161.5 | 6 | — |
| 10 | 162.2 | 5 | — |

The user data in Table 5 is the same as Table 3, except that there is a user report of "boredom." In this situation, the system may prompt the user to indicate changes the user would like to make. Based on this feedback, the system may select/recommend a diet change.

TABLE 5

| Day | Weight | Ketone Score | Symptom Card |
|---|---|---|---|
| 1 | 162.0 | 5 | — |
| 2 | 162.0 | 6 | — |
| 3 | 161.8 | 7 | — |

TABLE 5-continued

| Day | Weight | Ketone Score | Symptom Card |
|---|---|---|---|
| 4 | 163.2 | 8 | — |
| 5 | 161.5 | 5 | Medium Boredom |
| 6 | 161.2 | 5 | — |
| 7 | 161.0 | 6 | — |
| 8 | 160.8 | 5 | — |
| 9 | 161.5 | 6 | — |
| 10 | 160.5 | 5 | — |

The user data in Table 6 shows low ketone scores and also no weight loss. The symptom report also shows that the user has not adjusted to a well-formulated diet program. The system may, for example, classify this individual as being in a Fat Neutral phase with a 50% confidence level and a Fat Storage State with an 80% confidence level.

TABLE 6

| Day | Weight | Ketone Score | Symptom Card |
|---|---|---|---|
| 1 | 162.0 | 2 | High Hunger |
| | | | High Cravings |
| 2 | 162.0 | 3 | — |
| 3 | 161.8 | 1 | — |
| 4 | 163.2 | 0 | — |
| 5 | 162.0 | 2 | — |
| 6 | 161.5 | 1 | — |
| 7 | 162.3 | 3 | — |
| 8 | 162.0 | 2 | — |
| 9 | 161.5 | 1 | — |
| 10 | 162.2 | 2 | — |

The user data in Table 7 shows low ketone scores but also shows weight loss. The system may prompt this user for signs of dehydration, increased coffee consumption, stopping an exercise program or other things that could cause a weight loss without commensurate high ketones. However, ketone levels vary from person to person. The symptom report showing that the user is "feeling great" reflects that the user may just have low ketone levels (including a "0"), but is losing weight. The system may classify this user as being in a Fat Burn phase with a 60% confidence, but may update this classification if weight loss does not continue.

TABLE 7

| Day | Weight | Ketone Score | Symptom Card |
|---|---|---|---|
| 1 | 162.0 | 2 | Feels Great! |
| 2 | 162.0 | 3 | — |
| 3 | 161.8 | 1 | — |
| 4 | 163.2 | 0 | — |
| 5 | 161.5 | 2 | — |
| 6 | 161.2 | 1 | — |
| 7 | 161.0 | 3 | — |
| 8 | 160.8 | 2 | — |
| 9 | 161.5 | 1 | — |
| 10 | 160.5 | 2 | — |

Presentation of Program Recommendations

To recommend a program (such as an exercise/diet program) to a user, the system may either pick a single program or give the user a choice between programs. (Each program typically includes a diet, and may also prescribe specific exercise activities.) If the user is given an option to select between program options, the program options are preferably presented in a ranked order to increase the likelihood that the user will select a top-ranked program, and the user's selection is recorded by the system. The program rankings may, for example, be based on rules that score the programs based on the user's data record. The following are examples of types of such program scoring rules: (1) if current diet is ineffective, score programs with more extreme diets higher, (2) if user is non-compliant, score "easier" diets higher, (3) if the user has unsuccessfully used the program previously, score the program lower.

The program rankings may also or alternatively be based on a predictive scoring scheme that scores candidate programs in terms of their predicted effectiveness for the particular user based on the data of other users. As one example, a collaborative filtering engine may score each candidate program in terms of how effective that program has been (based on the data collected by the system) for users having profiles similar to that of the target user. Any programs that the target user has already used unsuccessfully may be filtered from the ranked list (or lowered in rank) before the list is presented to the user.

Various options are available for controlling the timing with which program recommendations are provided to a user. For example, the system 40 may be designed to generate a new program recommendation for a user (1) when the user explicitly requests a new program, (2) periodically, (3) whenever the user's classification changes to "ineffective" or "non-compliant," or (4) a combination of the foregoing.

Use Case Examples

The following use case examples illustrate user-system interactions for hypothetical users, and illustrate how users may be classified in terms of program effectiveness.

Bob—A Typical User

Bob starts using the system 40 to lose weight. He has gained weight consistently since high school and has over a hundred pounds to lose. The system (via the mobile application) initially assigns a standard low carb diet to Bob without giving him any other choices. He starts monitoring his ketone level with breath analysis device 30 and mobile application 32, and quickly generates sustained ketone scores of over 4. The system classifies Bob's program as "effective" and does not recommend any further changes.

Three weeks later and after losing 20 pounds, Bob's weight loss starts to slow. Additionally, Bob has indicated through the mobile application's UI that he is "unhappy" with the program and "wants to have quicker results." In response to Bob's indications, a rule in the rules database 46 causes his program classification to be changed from "effective" to "unhappy." Because this rule triggers a change in program classification, another rule (which is scheduled to run on any program classification change) runs and recommends a more "extreme" diet. Following this rule, the only "extreme" diet after the standard low carb diet is a fat fast. Through the mobile application, the system then provides Bob with the following ranked list of diet options: (1) fat fast; (2) continue on regular diet; (3) switch out common foods so there is more diversity.

Bob declines to use the fat fast because of other concerns and informs the mobile application that he will continue with the same diet. The system then follows a rule that classifies Bob as "off the beaten track" and notifies his human coach. The coach looks at Bob's results and realizes that Bob's expectations are unrealistic. The coach uses the system 40 to prepare an anonymized report of aggregated diet trends showing that Bob's progress is normal, and provides this report to Bob. (The system 40 could alternatively generate and provide such a report without coach intervention.) The coach indicates to the system (e.g., through a coach version of the mobile application) that a manual intervention was taken.

Over the next couple of weeks, Bob starts making more progress. Also, his indications of being unhappy slow and eventually drop off. Instead, during his weekly questionnaires presented by the mobile application, Bob starts indicating that he is happy again. A classification rule in the system responds by causing Bob's classification back from "unhappy" to "effective."

Two weeks later, the system 40 sends an email to the coach reminding the coach of the intervention, and informing the coach of successful results. This email is triggered by a rule that searches for a coach intervention followed by a positive change in state that is sustained for two weeks. In response, the coach adds a rule that causes users who are unhappy but are unwilling to adopt an extreme diet to, if applicable, be presented an anonymized report showing that their progress is normal compared to other users.

Sally—A Non-Compliant User

Sally starts using the system 40 and obtains ketone scores of 8-10 after her first week. She continues to get good scores but then starts cheating on her diet after two weeks. When she cheats, her ketone scores drop below 4. The system, via a pattern detection rule, detects a pattern in which ketone scores are above 4 but then sharply decline below 4. Following this rule, the system 40 instantiates an automated calibration procedure on the breath analysis device, and this procedure shows that the device is working correctly. The system, following its rules, then changes Sally's classifications from "effective" to "non-compliant".

In response to the classification change, the system follows a rule to pick a behavioral modification. A trained SVM model indicates that sending reminders before lunch and before sleep will be useful. Sally's profile indicates that she usually goes to sleep at about 10 μm. The system then reminds Sally (e.g., via the mobile application 32 or a text message) at 9 PM each evening not to eat anything unnecessary.

This works briefly but then Sally continues cheating, and her classification is not changed. Ultimately, the system learns that the notifications were not effective, and discontinues their use for Sally. The next time the SVM model is trained, assuming Sally's data is part of the training set, the system may rely on Sally's data to update its rules to reduce or eliminate it reliance on the rule that caused the reminders to be presented.

After detecting that the reminders were ineffective for Sally, the system 40 follows a rule that causes a collaborative filtering component to be used to select a diet for the non-compliant participant. (The following section describes one embodiment of a collaborative filtering algorithm that can be used for this purpose.) To select the diet, the system matches Sally to users with similar profiles but who have obtained successful results, and based on the programs successfully followed by these users, generates five diet suggestions for Sally. Sally selects one of the five diet options and records her selection via the mobile application. The system also provides an option (with consent of the other users) for Sally to communicate through the mobile application with the similar users who successfully followed the selected diet option.

Sally is happy with the new diet suggestion, and the feedback she provides to the system over a period of two weeks causes the system to update her classification to "effective."

Figure 6:
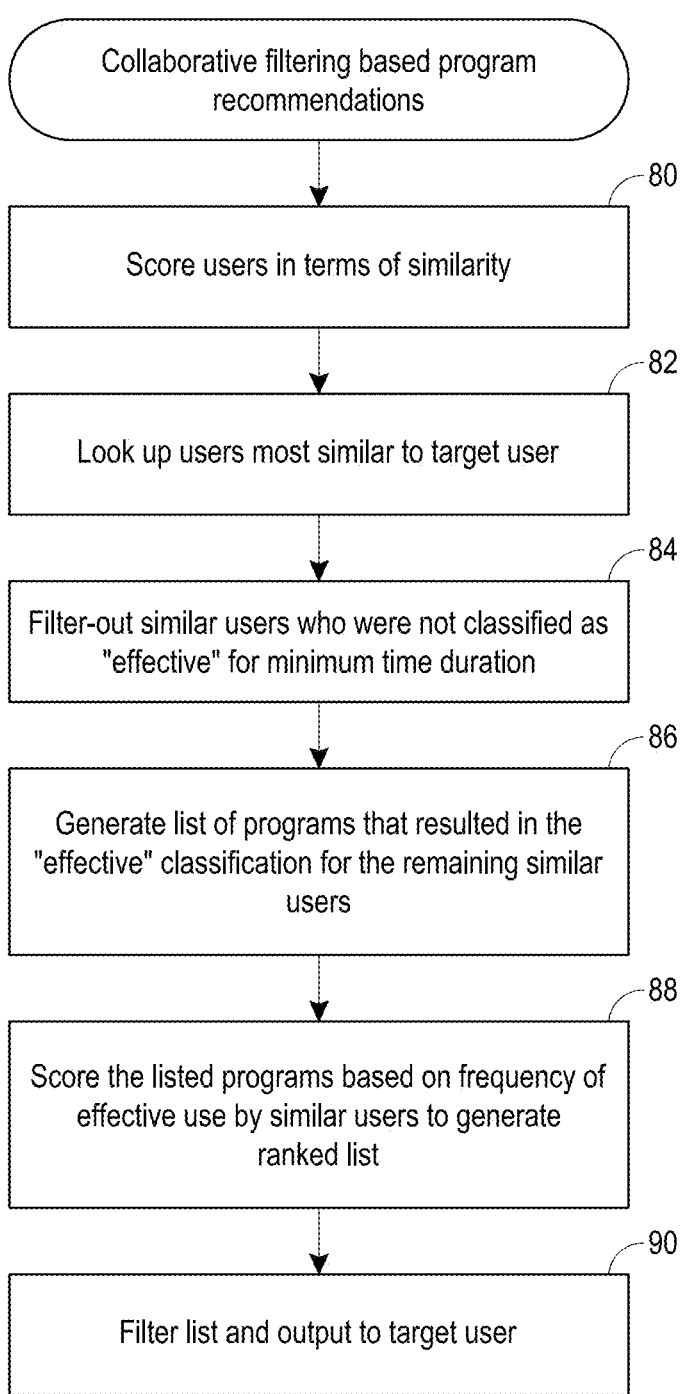
FIG. 6 illustrates a collaborative filtering algorithm that may be used to generate health program recommendations.

Collaborative Filtering Algorithm (FIG. 6)

FIG. 6 illustrates a collaborative filtering algorithm and process that can be used to generate program recommendations for users of the system. This algorithm may, for example, be implemented by the classifier/recommender of 42 of FIG. 5, or by a separate recommendation engine (not shown) of the system 40.

In block 80 of FIG. 6, the process scores pairs of users in terms of their similarity to one another. This step may be performed periodically (e.g., once per day or once week) as an off-line task. User similarity is preferably measured by comparing the data records 44 of the users while giving different amounts of weight to different attributes or features. For example, age, gender, weight, weight loss goals, psychological profile (if known) and ketone score history may be given relatively high amounts of weight for purposes of calculating user similarity. Other attributes or features, such as those related to the number of missed or window-aberrant ketone measurements, may be given relatively little or no weight. The result of block 80 may be a data structure that maps each user to the N most similar users (where N is a selected value such as 20, 50 or 100). The associated similarity scores may be stored in this data structure.

In addition to being used to provide program recommendations, the user similarity determinations of block 80 may be used for social networking purposes. For example, the system 40 could use the user similarity mappings to suggest or create social network connections between similar users. These social network connections can then be used to enable the connected users to, e.g., communicate with each other via the mobile application 32.

The remaining steps, shown in blocks 82-90 of FIG. 6, may be triggered by an event and associated rule that causes collaborative program recommendations to be generated for a particular user, referred to herein as the "target user" (see "Sally" example above). In block 82, the process looks up the users determined to be the most similar to the target user. In block 84, the process filters out from this "similar users" list any users who did not attain and maintain an "effective" or similar classification for a threshold period of time, such as 2 weeks or 4 weeks. In block 86, the process generates a list of the programs (e.g., weight loss programs or other health programs) that produced the sustained effective classifications for these similar users.

In block 88, the process ranks the list of programs by scoring the programs in terms of predicted effectiveness for the target user. In one embodiment, each program is scored in terms of its frequency of effective use (e.g., how many similar users used it effectively). However, other factors may additionally or alternatively be considered. For example, effective use by a user who is highly similar to the target user may be given more weight than effective use by a less similar user. Further, the duration of effective use by the similar users may be considered.

In block 90, the ranked list is filtered and then output for presentation to the target user. The filtering may involve removal of any programs that have already been used unsuccessfully by the target user or that conflict with dietary or exercise restrictions of the target user. As an alternative to completely filtering out such programs, they may be lowered in rank.

Behavioral Modifications for Non-Compliant Users

In some embodiments, the system 40 may take one or more types of actions to attempt to correct the behaviors of users identified as "non-compliant." The following are examples of such actions: (1) send time-based notifications to user reminding user not to eat during critical parts of the day, (2) send location-based notifications reminding user (e.g., reminding user not to eat certain things when the system detects that the user is at a restaurant), (3) prompt the user to log their diet, (4) asking the user's coach, or a member of the user's social network, to perform an intervention or otherwise provide support. These and other actions may be specified by a set of rules that are triggered by a transition to the "non-compliant" classification.

Coding of Rules

As described above, rules may be used both to classify the users and to generate the messaging (such as program recommendations) for the users and their human coaches. The rules can be hard coded into the business logic of the classifier 42 and/or the mobile application 32. However, this limits the flexibility of the system and the ease in which new rules are added. Thus, the rules are preferably stored instead in a relational databased 46, preferably as respective rows. Each such rule can preferably be dynamically enabled or disabled by updating the database 46.

In some embodiments, each rule is stored as source code in an existing programming language. To run the rule, the classifier (or some other component) fetches it from the database 46 and executes the code dynamically. Certain programming languages like Javascript, Ruby, and Python make it easy to dynamically execute code. However, using actual source code is not always desirable because it requires the users that input the rules (who usually are domain experts and not programming experts) to write software code. An alternative is to use a domain specific programming language (DSL). These tend to be languages that are less expressive and "powerful," designed for domain experts rather than software engineers.

In other embodiments, some or all of the rules are implemented as conditional statements that are specified without the use of a programming language. To implement a conditional statement in one embodiment, the database includes (1) an "expression" column used to look up a certain value; (2) an "operation" column that denotes equals, greater than, less than, etc.; and (3) a "match" value. When the expression matches the match value, the rule is triggered and executed. This basic model can be enhanced by allowing Boolean combinations of conditional expressions with "AND", "OR", and "NOT" logic.

Typically, the rules are deterministic, but they do not need to be. Rules can be randomized or leverage other learning techniques. For example, a rule may be "try to predict the user's insulin tolerance and then do X otherwise do Y."

Example User Interface Screens

FIGS. 7-10 illustrate example screen displays of one embodiment of the mobile application 32.

Figure 7:
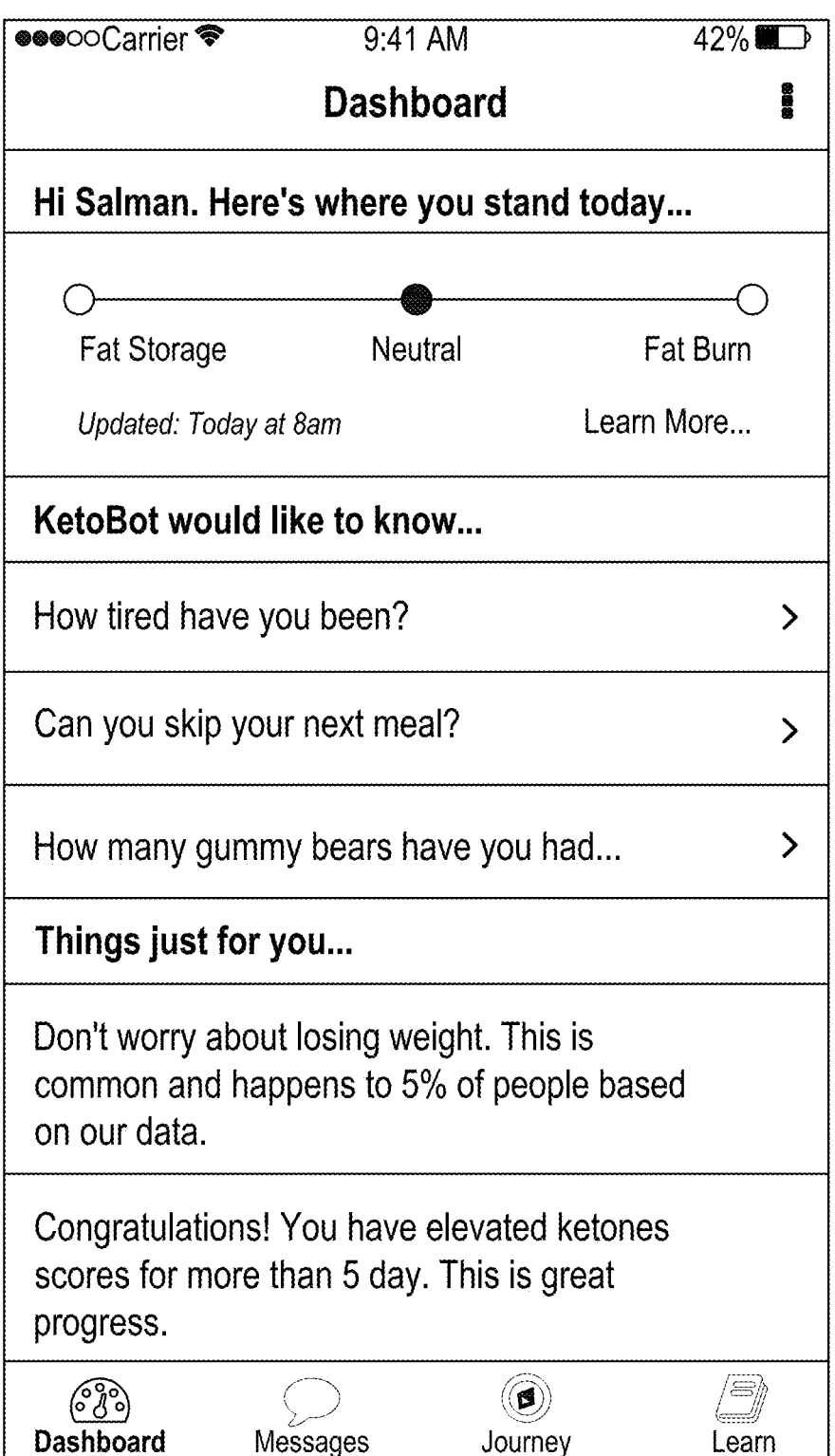
Figure 8:
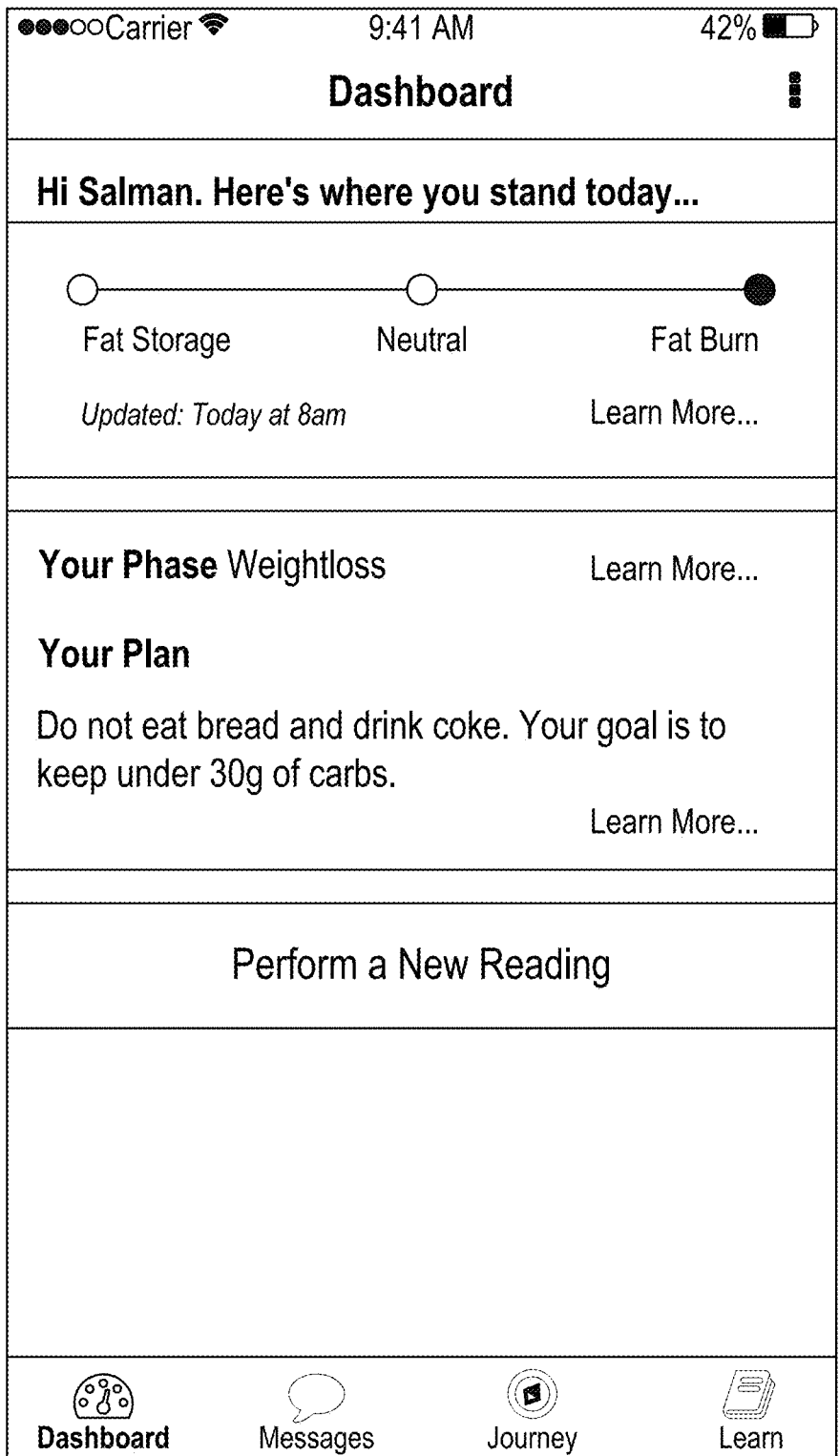

FIGS. 7 and 8 show views of a "dashboard" section of the mobile application 32. Both views include an indication of the current weight loss phase or classification of the user (fat storage, neutral, or fat burn). The view in FIG. 7 also includes a personalized set of questions for the user. The user's answers to these questions may be used by the system 40 to reclassify the user and to make associated behavioral (e.g., health program) recommendations. The view in FIG. 7 also includes a "things just for you" section with auto-selected messaging regarding the user's progress. The view in FIG. 8 also includes an indication of the weight loss program or "plan" currently assigned to the user, and includes an option to perform a new ketone reading.

FIG. 9 illustrates a "journey" section of the mobile application. The illustrated view includes auto-generated messaging regarding the rate at which the user is losing weight in comparison to other users of the system. The view also indicates that the system 40 has detected that the user is sensitive to diet products. The view also includes a timeline showing phases and events of the user since inception. The timeline shows that the user was initially in a "calibrating" phase in which the system determined the rate at which the user's ketone levels changed once the user started a low-carb diet, as discussed above with reference to FIGS. 2A-2D. The timeline also indicates weight loss events.

Figure 10:
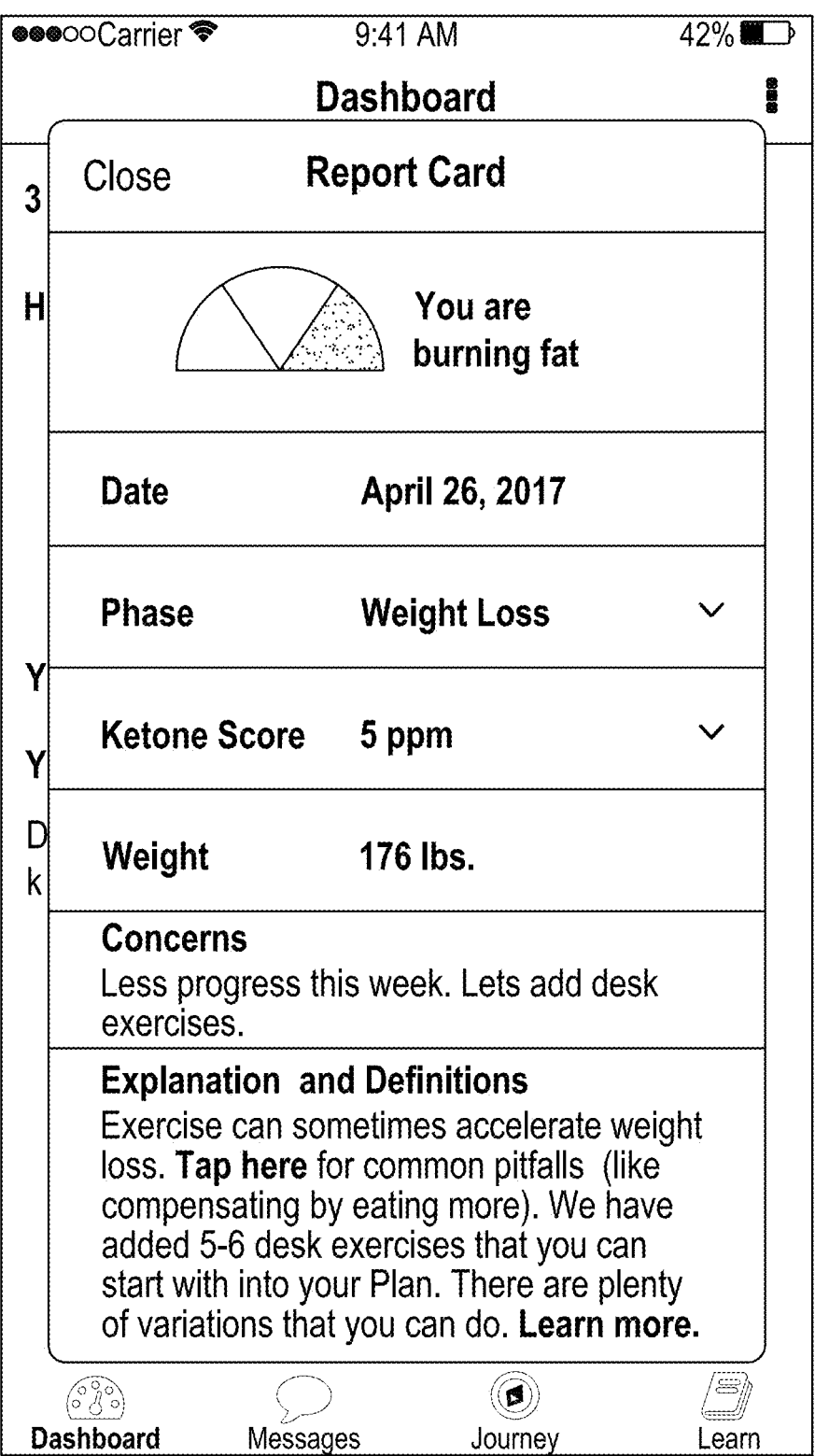

FIG. 10 illustrates a "report card" view that enables users to track their progress. The scorecard may be updated when, for example, the user completes the three daily tasks mentioned above, namely measuring their weight, measuring their ketone score, and answering a set of questions. The report card shows the user's current fat gain/loss phase (shown as "fat burn" in this example), program phase, ketone score, and weight. The "concerns" section includes auto-selected messaging related to the user's progress and to any auto-selected program modifications. The "explanations and definitions" section displays educational content that is auto-selected based on the user's current state.

CONCLUSION

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others.

What is claimed is:

1. A system capable of using artificial intelligence to provide health coaching based on breath analyte levels of users, the system comprising:
  a plurality of portable breath analysis devices, each breath analysis device comprising a sensor capable of measuring levels of a breath analyte that correlates with fat metabolism, the portable breath analysis devices configured to generate breath analyte measurements of the breath analyte based on breath samples of users, the breath analyte measurements reflective of effectiveness levels of current health programs assigned to the users, each breath analysis device comprising a wireless transceiver capable of wirelessly transmitting the breath analyte measurements of the users; and a computing system that hosts an automated health coaching system, the automated health coaching system configured to use a machine learning process to classify the users based, at least partly, on data records of the users, the data records including the breath analyte measurements of the users and including other profile data of the users, the automated health coaching system further configured to use at least the classifications to select health program modifications, including diet modifications, for particular users, and to output an indication of the selected health program modifications for display via a user interface, the computing system comprising one or more physical servers;

wherein the computing system is programmed with executable instructions to use a trained model to classify the users based on the data records of the users, the trained model comprising (1) a feature extractor that extracts features from the data records of the users, the features including features based on the breath analyte measurements and other profile data of the users, and (2) a classifier that classifies the users using a set of weights that specify amounts of weight to apply to particular extracted features, the weights learned by applying a machine learning algorithm to classified user data records;

wherein the computing system uses the trained model to assign a particular user to at least one first classification at a first time and reassign the particular user to at least one second classification at a second time subsequent to the first time, the reassignment being performed responsive to receiving a new breath analyte measurement of the particular user; and wherein the computing system is programed to include a supervised feedback loop configured to receive feedback from a human expert indicating whether or not the trained model correctly classified the users in the at least one first or second classification, and iteratively updating the trained model based on the received indication from the human expert, thereby continually improving the quality of the trained model.

2. The system of claim 1, wherein the automated health coaching system is configured to assign to a user a classification that represents an effectiveness of a current health program assigned to the user.

3. The system of claim 1, wherein the automated health coaching system is configured to assign to a user a classification representing a rate at which the user's breath analyte measurements increase in response to placement of the user on a particular diet.

4. The system of claim 1, wherein the automated health coaching system is configured to assign multiple concurrent classifications to a user.

5. The system of claim 1, wherein the automated health coaching system comprises a data repository of rules, including a rule that specifies an action to be performed in response to a change in a classification of a user.

6. The system of claim 5, further comprising an adaptive refinement component that adaptively modifies the data repository of rules based on feedback data reflective of effectiveness levels of the rules on health conditions of the users.

7. The system of claim 1, wherein the automated health coaching system is programmed to use a collaborative filtering algorithm to select health programs to recommend to users, the collaborative filtering algorithm configured to select, for a target user, at least one health program that has produced effective results for users identified as being similar to the target user.

8. The system of claim 1, further comprising a mobile application that runs on mobile devices of the users, the mobile application configured to enable a mobile device of a user to (1) communicate wirelessly with a breath analysis device of the user, and (2) communicate with the computing system, the mobile application further configured to display to the user health program modifications selected by the automated health coaching system for the user.

9. The system of claim 8, wherein the mobile application is configured to prompt the user for information regarding an effectiveness of a current health program, and the automated health coaching system is programmed to use the information to classify the user.

10. The system of claim 8, further comprising a wireless scale, the wireless scale comprising a wireless transceiver and being configured to report weight measurements to the mobile application.

11. The system of claim 10, wherein the system is programmed to use at least weight measurements generated with the wireless scale, in combination with breath analyte measurements generated by a breath analysis device, to classify a user in terms of whether the user is burning fat.

12. The system of claim 1, wherein the computing system is configured to adaptively adjust the weights based on monitored health program results resulting from the user classifications and the selected health program modifications.

13. The system of claim 1, wherein the classified user data records are human-expert-classified user data records.

14. The system of claim 1, wherein the classifier comprises sub-classifiers, and is capable of classifying a user such that the user is concurrently classified into multiple classifications.

15. The system of claim 1, wherein the trained model includes a plurality of classifiers, including a first classifier used to select a first type of health program modification and a second classifier used to select a second type of health program modification.

16. The system of claim 1, wherein the feature extractor is configured to generate a feature that is based on a plurality, but less than all, breath analyte measurements included in a data record of a user.

17. A system capable of using artificial intelligence to provide health coaching based on breath analyte levels of users, the system comprising:

a plurality of portable breath analysis devices, each breath analysis device comprising a sensor capable of measuring levels of a breath analyte that has a correlation with fat metabolism, the portable breath analysis devices configured to generate breath analyte measurements of the breath analyte based on breath samples of users, the breath analyte measurements reflective of effectiveness levels of current health programs assigned to the users, each breath analysis device comprising a wireless transceiver capable of wirelessly transmitting the breath analyte measurements of the users;

a data repository that stores data records of respective users of the portable breath analysis devices, the data records including breath analyte measurements generated by the portable breath analysis devices, including measurements of said breath analyte that has a correlation with fat metabolism, the breath analyte measurements reflective of effectiveness levels of current health programs assigned to the users, the data records additionally including other profile data of the users; and a computing system programmed to use a trained machine learning model to classify users based on the respective data records of the users, the trained machine learning model comprising (1) a feature extractor that extracts features from the data records of the users, including features that are based on the breath analyte measurements and other profile data of the users, and (2) a classifier that assigns classifications to the users using a set of weights that specify amounts of weight to apply to particular extracted features, the weights learned by applying a machine learning algorithm to classified user data records;

wherein the computing system is configured to apply a clustering algorithm to the user data records to search for new classifications, wherein the clustering algorithm generates 2K clusters, where K is the current number of classifications, and generates a report that enables an administrator to assess whether any of the clusters should be converted into a new classification; and wherein the computing system is configured to use the assigned classifications to select health program modifications for particular users, and output an indication of the selected health program modifications for display via a user interface.

18. The system of claim 17, wherein the trained machine learning model further comprises:

a transactional queue of user classification tasks to be executed, and a scheduler that adds the user classification tasks to the transactional queue.

19. The system of claim 18, wherein the computing system comprises a plurality of machines that pull the user classification tasks from the transactional queue and process the pulled user classification tasks.

20. The system of claim 17, wherein the computing system comprises a data repository of rules, including rules that specify an action to be performed in response to a change in a classification of a user.

21. The system of claim 17, wherein the breath analyte that has a correlation with fat metabolism is a breath ketone.

* * * * *